(12) United States Patent
Horvath et al.

(10) Patent No.: US 11,820,789 B2
(45) Date of Patent: Nov. 21, 2023

(54) GLYCOSYLATED SPHINGOID BASES AND PRODUCTION THEREOF

(71) Applicant: CarboCode S.A., Cantanhede (PT)

(72) Inventors: Ferenc Horvath, Pilisszentkereszt (HU); Györgyi Osztrovszky, Kisvarda (HU); Gyula Dekany, Sinnamon Park (AU); Andras Nagy, Komlo (HU); Piroska Kovacs-Penzes, Jaszbereny (HU); Jorge Santos, Alenquer (PT)

(73) Assignee: CarboCode S.A., Cantanhede (PT)

(*) Notice: Subject to any disclaimer, the term of this patent is extended or adjusted under 35 U.S.C. 154(b) by 186 days.

(21) Appl. No.: 17/251,945

(22) PCT Filed: Jun. 14, 2019

(86) PCT No.: PCT/EP2019/065779
§ 371 (c)(1),
(2) Date: Dec. 14, 2020

(87) PCT Pub. No.: WO2019/238965
PCT Pub. Date: Dec. 19, 2019

(65) Prior Publication Data
US 2021/0332077 A1 Oct. 28, 2021

(30) Foreign Application Priority Data
Jun. 15, 2018 (DE) .................. 10 2018 114 376.1

(51) Int. Cl.
| | |
|---|---|
| *C07H 15/04* | (2006.01) |
| *C07H 1/00* | (2006.01) |
| *C07H 15/26* | (2006.01) |
| *A23L 33/125* | (2016.01) |
| *A61K 8/60* | (2006.01) |
| *A61Q 19/00* | (2006.01) |
| *C07D 239/60* | (2006.01) |

(52) U.S. Cl.
CPC ............ *C07H 15/26* (2013.01); *A23L 33/125* (2016.08); *A61K 8/602* (2013.01); *A61Q 19/00* (2013.01); *C07D 239/60* (2013.01); *C07H 1/00* (2013.01); *C07H 15/04* (2013.01); *A23V 2002/00* (2013.01)

(58) Field of Classification Search
CPC .......................... C07H 15/04–10; C07H 1/00
See application file for complete search history.

(56) References Cited

U.S. PATENT DOCUMENTS

| | | | |
|---|---|---|---|
| 6,462,183 B1 | 10/2002 | Toth et al. | |
| 2003/0171621 A1 | 9/2003 | Van Boom et al. | |
| 2017/0029454 A1* | 2/2017 | Teyton | A61K 39/02 |

FOREIGN PATENT DOCUMENTS

| | | |
|---|---|---|
| EP | 1452520 A1 | 9/2004 |
| WO | 9838197 A1 | 9/1998 |

OTHER PUBLICATIONS

Chaudhari et al., "An Efficient Synthesis of D-erythro-and D-threo-Sphingosine from d-Glucose: Olefin Cross-Metathesis Approach", Org. Lett., 2005, pp. 5805-5807, vol. 7, No. 26.

(Continued)

*Primary Examiner* — Bahar Craigo
(74) *Attorney, Agent, or Firm* — Neal, Gerber & Eisenberg LLP

(57) ABSTRACT

The present invention relates to several novel 1-O-glycosylated sphingoid bases and to a production method thereof, as well as to uses of the 1-O-glycosylated sphingoid bases. Sphingoid bases carrying a vinylogous amide-type protecting group are used herein for the production of 1-O-glycosylated sphingoid bases. These vinylogous amide compounds enable an easy and effective production of 1-O-glycosylated sphingoid bases.

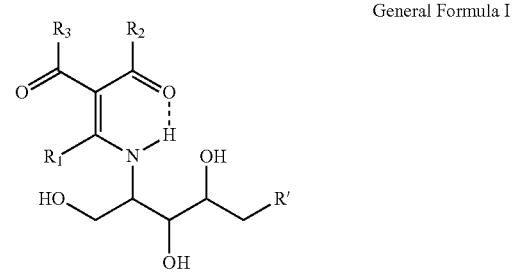

General Formula I

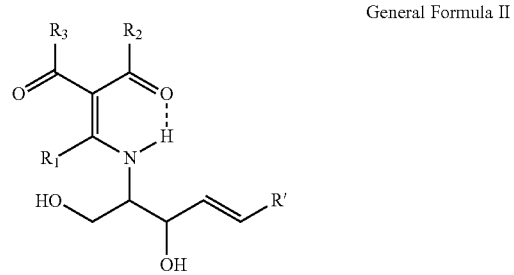

General Formula II

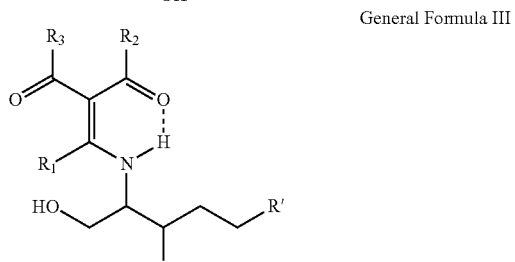

General Formula III

18 Claims, No Drawings

(56) References Cited

OTHER PUBLICATIONS

Dekany et al., "A novel amino protecting group: DTPM", Tetrahedron Letters, 2001, pp. 3129-3132, vol. 42, No. 17.

Di Benedetto et al., "Protected sphingosine from phytosphingosine as an efficient acceptor in glycosylation reaction", Org. Lett., 2014, pp. 952-955, vol. 16, No. 3.

Abraham et al., "Asymmetric synthesis of vicinal amino alcohols: xestoaminol C, sphinganine and sphingosine", Org. Biomol. Chem., 2008, pp. 1655-1664, vol. 6.

Gao et al., "Recent progress in chemical syntheses of sphingosines and phytosphingosines", Synthesis, 2016, pp. 4017-4037, vol. 48, No. 23.

Ha et al., "Synthesis of D-erythro-Sphingosine from D-ribo-Phytosphingosine", Bull. Korean Chem. Soc., 2009, pp. 535-536, vol. 30, No. 3.

Kim et al., "Efficient Synthesis of D-erythro-Sphingosine and D-erythro-Azidosphingosine from D-ribo-Phytosphingosine via a Cyclic Sulfate Intermediate", J. Org. Chem., 2006, pp. 8661-8664, vol. 71, No. 22.

Llaveria et al.,"An efficient and general enantioselective synthesis of sphingosine, phythosphingosine, and 4-substituted derivatives", Org. Lett., 2009, pp. 205-208, vol. 11, No. 1.

Merino et al., "Enantiodivergent Synthesis of d-and l-e rythro-Sphingosines through Mannich-Type Reactions of N-Benzyl-2, 3-O-isopropylidene-d-glyceraldehyde Nitrone", J.Org. Chem., 2006, pp. 4685-4688, vol. 71, No. 12.

Morales-Serna et al.,"Synthesis of D/L-erythro-Sphingosine Using a Tethered Aminohydroxylation Reaction as the Key Step", Synthesis, 2009, pp. 710-712, vol. 5.

Murakami et al., "Regio-and stereocontrolled synthesis of d-erythro-sphingosine and phytosphingosine from d-glucosamine", Tetrahedron Lett., 1994, pp. 745-748, vol. 35, No. 5.

Shinozaki et al., "Synthesis of D-erythro-Sphingosine from D-Glucosamine", Chem. Pharm. Bull., 1996, pp. 927-932, vol. 44, No. 5.

Sridhar et al., "Asymmetric synthesis of triacetyl-d-erythro-sphingosine and D-1-deoxyallonojirimycin via Miyashita C2 selective endo-mode azide opening of 2,3-epoxy alcohol", Tetrahedron, 2009, pp. 10701-10708, vol. 65, No. 51.

Van den Berg et al.,"A simple and low cost synthesis of D-erythro-sphingosine and D-erythro-azidosphingosine from D-ribo-phytosphingosine: glycosphingolipid precursors", Tetrahedron Lett., 2002, pp. 8409-8412, vol. 43, No. 46.

Van den Berg et al., "Effective, High-Yielding, and Stereospecific Total Synthesis of D-erythro-(2 R, 3 S)-Sphingosine from D-ribo-(2 S, 3 S, 4 R)-Phytosphingosine", J. Org. Chem., 2004, pp. 5699-5704, vol. 69, No. 17.

Wild et al., "Sphingosine and phytosphingosine from D-threose synthesis of a 4-keto-ceramide", Tetrahedron: Asymmetry, 1994, pp. 2195-2208, vol. 5, No. 11.

Wisse et al., "Synthesis of 6-Hydroxysphingosine and a-Hydroxy Ceramide Using a Cross-Metathesis Strategy", J. Org. Chem., 2015, pp. 7258-7265, vol. 80, No. 14.

Yang et al., "Concise and Scalable Synthesis of High Enantiopurity (−)-D-erythro-Sphingosine Using Peptidyl Thiol ster-Boronic Acid Cross-Coupling", Org. Lett., 2007, pp. 2993-2995, vol. 9, No. 16.

Morales-Serna et al.,"Recent advances in the glycosylation of sphingosines and ceramides", Carbohydrate Research, 2007, pp. 1595-1612, vol. 342.

Rich et al., "Glycosphingolipid synthesis employing a combination of recombinant glycosyltransferases and an endoglycoceramidase glycosynthase", Chem. Commun., 2011, pp. 10806-10808, vol. 47.

Santra et al., "Highly efficient chemoenzymatic synthesis and facile purification of a-Gal pentasaccharyl ceramide Gal+3nLc4βCer", Chemical Communications (Camb), 2017, pp. 8280-8283, vol. 53, No. 59.

* cited by examiner

GLYCOSYLATED SPHINGOID BASES AND PRODUCTION THEREOF

CROSS-REFERENCE TO RELATED APPLICATIONS

This application is the United States national phase of International Application No. PCT/EP2019/065779 filed Jun. 14, 2019, and claims priority to German Patent Application No. 10 2018 114 376.1 filed Jun. 15, 2018, the disclosures of each of which are hereby incorporated by reference in their entireties.

BACKGROUND OF THE INVENTION

Field of the Invention

The present invention relates to sphingolipids, and more particularly to a novel method for the production of glycosylated sphingoid bases and derivatives thereof.

Related Art

Sphingoid bases are chiral, long-chain aminoalcohols representing the most essential structural constituents of sphingolipids including glycosphingolipids. Structural analysis of eukaryotic plasma and organelle sphingolipid membrane components have demonstrated the presence of over one hundred different sphingoid bases in Nature. More structural diversity of sphingoid bases were added recently, when prokaryotic sphingolipids and their related sphingoid bases were found in large quantities in human intestinal microbiota. Sphingoid bases can be modified by N-acylation processes forming functional lipids such as ceramides, dihydroceramides, phytoceramides, etc., furthermore, they can also be glycosylated at their 1-O-positions leading to glycosylated sphingoid bases. In living systems, glycosylated sphingoid bases are usually formed by metabolic processes of more complex glycosphingolipids.

The aliphatic chains of sphingoid bases can contain 14 to 27 carbon atoms, and they can be saturated, mono-unsaturated and di-unsaturated, with double bonds of either in cis or trans configuration. Sphingoid bases, even with three double bonds, have also been found. In addition, long-chain bases can have branched chains with alkyl substituents and can further be substituted by hydroxyl groups, ethoxy groups and even with cyclopropyl moieties.

Sphingoid bases and glycosylated sphingoid bases—due to their relatively high solubility—can cross membranes or move between membranes with relative ease. Thus, sphingoid bases and their glycosylated counterparts own great stabilities, bioavailabilities and bioactivities.

A large number of biologically important sphingolipids are characterized by substituted sphingoid base structures where the sphingoid bases are linked via amino groups to fatty acids to form ceramides, while polar head groups are attached to the primary hydroxyl moieties to produce more complex glycosphingolipids and phosphosphingolipids.

Sphingoid bases, their N-acylated forms such as ceramides, dihydroceramides and phytoceramides, glycosylated sphingoid bases, glycosylated-ceramides, glycosylated-dihydroceramides and glycosylated-phytoceramides are highly bioactive compounds suitable for cosmetic, nutritional, dietary supplement and pharmaceutical applications. Product demands coming from these industries have been significant for decades. However, synthetic access to these highly potent biomolecules in commercial volumes has strongly been prevented by the lack of cheap and robust technologies capable to provide both sphingoid bases and their glycosylated forms.

Historically, glycosylated sphingoid bases could be produced only in small quantities via either chemical glycosylations (for example: Jose Antonio Morales-Sema, Omar Boutureira, Yolanda Diaz, M. Isabel Matheu and Sergio Castillon, Carbohydrate Research 2007, 342, 1595-1612) or by endoglycoceramidase-assisted enzymatic approaches (for example: Jamie R. Rich, Anna-Maria Cunningham, Michel Gilbert and Stephen G. Withers, Chem. Commun., 2011, 47, 10806-10808). Chemical glycosylation of sphingoid bases has been a challenging topic for decades due to the low nucleophilicities of 1-O-positions of sphingoid bases caused by strong hydrogen bond type interactions within the NH protons and the 1-O moieties. Traditional protecting group strategies provide strongly compromised glycosylation yields which are preventive for manufacturing technology developments.

To date, this problem has been approached via the use of 2-azido-2-deamino-sphingoid bases or N-phthaloyl/N-substituted phthaloyl protection of sphingoid bases as key chemical moieties of acceptor molecules (e.g. van Boom et al. *Tetrahedron Lett.* 2002, 43(46), 8409-8412; Panza et al. *Org. Lett.* 2014, 16, 952-955).

The preparation of 2-azido-2-deamino sphingoid bases requires the use of hazardous chemicals prone to initiate explosions during diazotransfer reactions. Additionally, selective reduction of the azide moieties is required beside the unsaturated features of sphingosines after successful glycosylations of 2-azido-2-deamino sphingoid base. Thus, the traditional azide-method is not straightforward and not suitable for industrial applications.

The substituted/unsubstituted phthaloyl sphingoid base-type acceptors represent another kind of synthetic difficulties due to significantly reduced yields related to their problematic protecting group introduction/cleavage features.

In fact, the conjugation of glycans to sphingoid bases represents a major scientific challenge. After a successful lipid—carbohydrate conjugation, extending the sugar chains of existing carbohydrate-sphingoid base conjugates is a relatively routine task leading to more complex molecular structures via enzymatic glycosylations (for example: Santra, Abhishek; Li, Yanhong; Yu, Hai; Slack, Teri J.; Wang, Peng George; Chen, Xi, Chemical Communications (Cambridge, United Kingdom) (2017), 53(59), 8280-8283).

Synthetic access to glycosylated sphingoid bases has especially been limited to structures related to human glycosylated sphingoid bases carrying D-erythro-sphingosine (CAS: 123-78-4; $C_{18}H_{37}NO_2$) (1), D-ribo-phytosphingosine (CAS: 388566-94-7; $C_{18}H_{39}NO_3$) (2), DL-erythro-Dihydrosphingosine (CAS: 3102-56-5; $C_{18}H_{39}NO_2$) (3) and 6-Hydroxy-D-<erythro-sphingosine (CAS: 566203-07-4; $C_{18}H_{37}NO_3$) (4) molecular scaffolds.

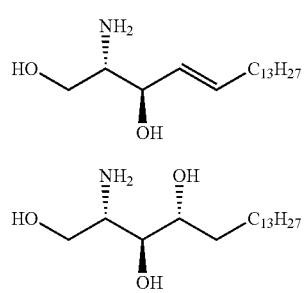

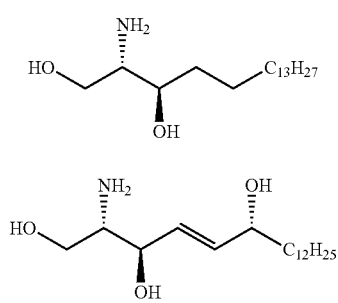

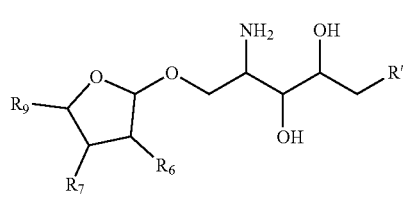

It is therefore an object of the present invention to provide glycosylated sphingoid bases in commercially interesting amounts and a method for their production, where the above-mentioned shortcomings are mitigated.

SUMMARY OF THE INVENTION (1) The invention provides a method for producing a glycosylated sphingoid base of General Formula XIX, XX, XXI, XXII, XXIII or XXIV, or a salt thereof:

General Formula XIX

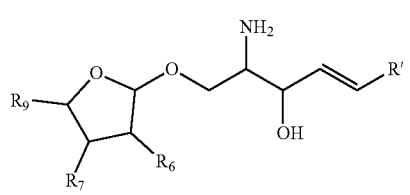

General Formuula XX

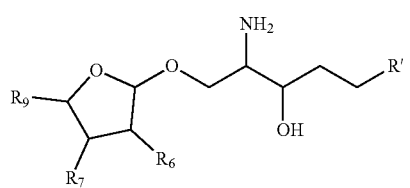

General Formula XXI

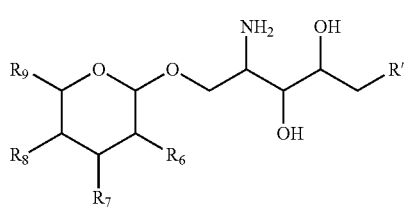

General Formula XXII

General Formula XXIII

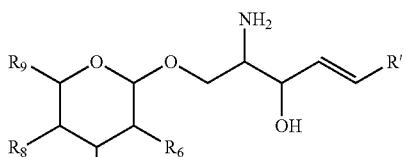

General Formula XXIV

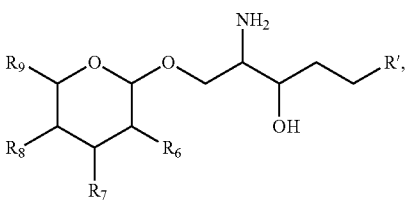

wherein
R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group, $R_6$ is H, OH, $NH_2$, $N_3$, NH-acyl or a carbohydrate moiety,
$R_7$ and $R_8$ are independently selected from H, OH and a carbohydrate moiety,
$R_9$ is H, $CH_3$, COOH, $CH_2OH$ or a $CH_2O$-carbohydrate moiety,
and
the dashed line ----- represents a hydrogen bond,
starting from a sphingoid base of General Formula I, II or III, wherein the sphingoid base has an N-protecting group, wherein the N-protecting group is a vinylogous amide-type N-protecting group:

General Formula I

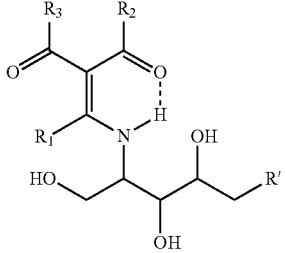

General Formula II

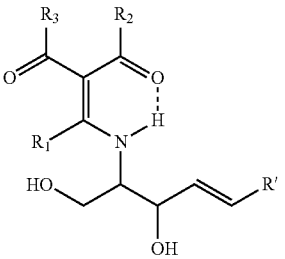

-continued

General Formula III

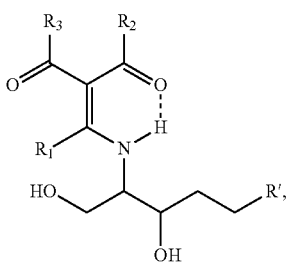

wherein
R' is as defined above,
$R_1$ is H, optionally substituted alkyl or optionally substituted aryl,
$R_2$ and $R_3$ are independently selected from optionally substituted alkyl, optionally substituted aryl, OR", NHR", NR"R'" wherein R" and R'" are independently H, optionally substituted alkyl or optionally substituted aryl, or wherein $R^2$ and $R^3$ form a cyclic structure characterized by a 5-8-membered ring,
and
the dashed line ----- represents a hydrogen bond,
this method comprising the steps of:
  a) Protecting the hydroxyl (OH) groups at $C_3$ and $C_4$ of General Formula I or at $C_3$ of General Formula II or III, respectively, with an O-protecting group, forming an O-protected compound,
  b) Reacting the O-protected compound of step (a) as an acceptor molecule with a carbohydrate donor, wherein the carbohydrate donor comprises an optionally substituted furanose or an optionally substituted pyranose ring, wherein the optionally substituted furanose ring or the optionally substituted pyranose ring is covalently linked via either an alpha- or a beta-glycosidic linkage to the $C_1$—O group of the acceptor molecule,
  c) Removing O-protecting group(s) from a compound formed in step (b),
  d) Removing N-protecting group(s) from a compound formed in step (c).

(2) The present invention further provides a compound of General Formula IV, especially obtainable by step (a) of the method of the present invention:

General Formula IV

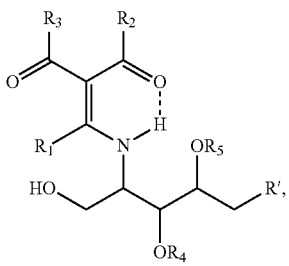

wherein
R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group,
$R_1$ is H, optionally substituted alkyl or optionally substituted aryl,
$R_2$ and $R_3$ are independently selected from optionally substituted alkyl, optionally substituted aryl, OR", NHR", NR"R'" wherein R" and R'" are independently H, optionally substituted alkyl or optionally substituted aryl, or wherein $R^2$ and $R^3$ form a cyclic structure characterized by a 5-8-membered ring,
$R_4$ and $R_5$ are independently selected from acyl, optionally substituted alkyl, optionally substituted acetal, optionally substituted ketal or silyl or wherein $R_4$ and $R_5$ form a cyclic structure
and
the dashed line ----- represents a hydrogen bond.

(3) Compound of General Formula V, especially obtainable by step (a) of the method of claim 1:

General Formula V

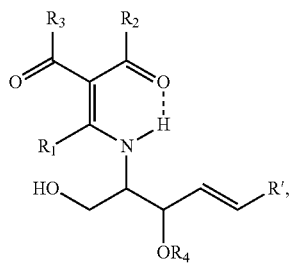

wherein
R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group,
$R_1$ is H, optionally substituted alkyl or optionally substituted aryl,
$R_2$ and $R_3$ are independently selected from optionally substituted alkyl, optionally substituted aryl, OR", NHR", NR"R'" wherein R" and R'" are independently H, optionally substituted alkyl or optionally substituted aryl, or wherein $R^2$ and $R^3$ form a cyclic structure characterized by a 5-8-membered ring,
$R_4$ is acyl, optionally substituted alkyl, optionally substituted acetal, optionally substituted ketal or silyl
and
the dashed line ----- represents a hydrogen bond.

(4) Compound of General Formula VI, especially obtainable by step (a) of the method of claim 1:

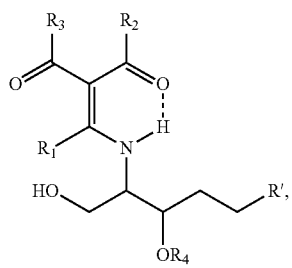

General Formula VI wherein

R', $R_1$, $R_2$, $R_3$ and $R_4$ are as defined in (3)

and the dashed line ----- represents a hydrogen bond.

(5) Compound of General Formula VII, especially obtainable by steps (a) to (b) of the method of claim 1:

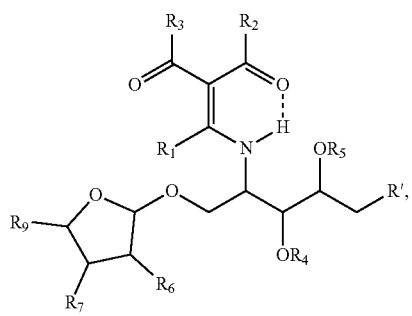

General Formula VII wherein

R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group, $R_1$ is H, optionally substituted alkyl or optionally substituted aryl, $R_2$ and $R_3$ are independently selected from optionally substituted alkyl, optionally substituted aryl, OR'', NHR'', NR''R''' wherein R'' and R''' are independently H, optionally substituted alkyl or optionally substituted aryl, or wherein $R^2$ and $R^3$ form a cyclic structure characterized by a 5-8-membered ring, $R_4$ and $R_5$ are independently selected from acyl, optionally substituted alkyl, optionally substituted acetal, optionally substituted ketal or silyl or wherein $R_4$ and $R_5$ form a cyclic structure, $R_6$ is O-acyl, $N_3$, NH-acyl, optionally substituted O-alkyl, O-carbohydrate moiety, O-silyl, optionally substituted acetal or optionally substituted ketal, $R_7$ is O-acyl, optionally substituted acetal, optionally substituted ketal, O-silyl, optionally substituted O-alkyl or an O-carbohydrate moiety, $R_9$ is H, $CH_3$, COOH, COOR'''' (where R'''' is optionally substituted alkyl) or $CH_2OR^V$, where $R^V$ is selected from acyl, optionally substituted alkyl, optionally substituted acetal, optionally substituted ketal, silyl or a carbohydrate moiety, and the dashed line ----- represents a hydrogen bond.

(6) Compound of General Formula VIII, especially obtainable by steps (a) to (b) of the method of claim 1:

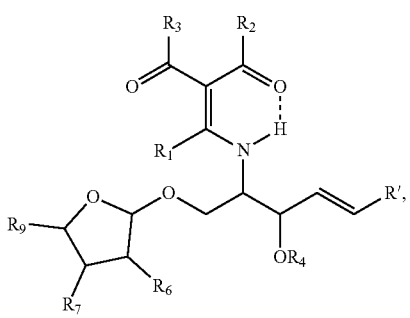

General Formula VIII wherein

R', $R_1$, $R_2$, $R_3$, $R_6$, $R_7$ and $R_9$ are as defined in (5), $R_4$ is acyl, optionally substituted alkyl, optionally substituted acetal, optionally substituted ketal or silyl, and the dashed line ----- represents a hydrogen bond.

(7) Compound of General Formula IX, especially obtainable by steps (a) to (b) of the method of claim 1:

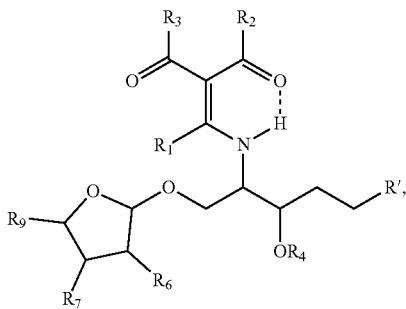

General Formula IX wherein

R', $R_1$, $R_2$, $R_3$, $R_4$, $R_6$, $R_7$ and $R_9$ are as defined in (5) or (6), and the dashed line ----- represents a hydrogen bond.

(8) Compound of General Formula X, especially obtainable by steps (a) to (b) of the method of claim 1:

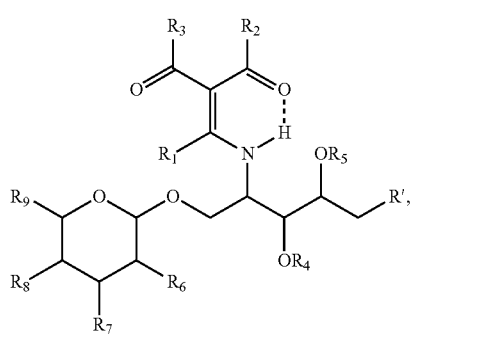

General Formula X wherein
- R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group,
- $R_1$ is H, optionally substituted alkyl or optionally substituted aryl,
- $R_2$ and $R_3$ are independently selected from optionally substituted alkyl, optionally substituted aryl, OR'', NHR'', NR''R''' wherein R'' and R''' are independently H, optionally substituted alkyl or optionally substituted aryl, or wherein $R^2$ and $R^3$ form a cyclic structure characterized by a 5-8-membered ring,
- $R_4$ and $R_5$ are independently selected from acyl, optionally substituted alkyl, optionally substituted acetal, optionally substituted ketal or silyl or wherein $R_4$ and $R_5$ form a cyclic structure,
- $R_6$ is O-acyl, $N_3$, NH-acyl, optionally substituted O-alkyl, O-carbohydrate moiety, O-silyl, optionally substituted acetal or optionally substituted ketal,
- $R_7$ and $R_8$ are independently selected from O-acyl, optionally substituted acetal, optionally substituted ketal, O-silyl, optionally substituted O-alkyl or an O-carbohydrate moiety,
- $R_9$ is H, $CH_3$, COOH, COOR'''' (where R'''' is optionally substituted alkyl) or $CH_2OR^V$, where $R^V$ is selected from acyl, optionally substituted alkyl, optionally substituted acetal, optionally substituted ketal, silyl or a carbohydrate moiety, and
- the dashed line ----- represents a hydrogen bond.

(9) Compound of General Formula XI, especially obtainable by steps (a) to (b) of the method of claim 1:

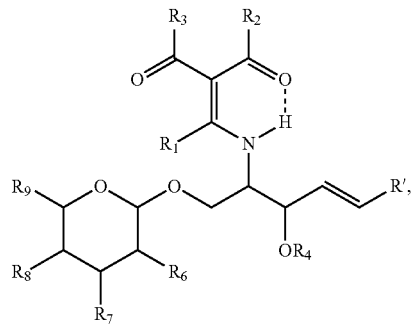

General Formula XI wherein
R', $R_1$, $R_2$, $R_3$, $R_6$, $R_7$, $R_8$ and $R_9$ are as defined in (8),
$R_4$ is acyl, optionally substituted alkyl, optionally substituted acetal, optionally substituted ketal or silyl, and
the dashed line ----- represents a hydrogen bond.

(10) Compound of General Formula XII, especially obtainable by steps (a) to (b) of the method of claim 1:

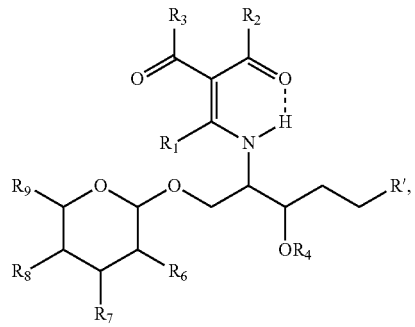

General Formula XII wherein
R', $R_1$, $R_2$, $R_3$, $R_4$, $R_6$, $R_7$, $R_8$ and $R_9$ are as defined in (9), and
the dashed line ----- represents a hydrogen bond.

(11) Compound of General Formula XIII, especially obtainable by steps (a) to (c) of the method of claim 1:

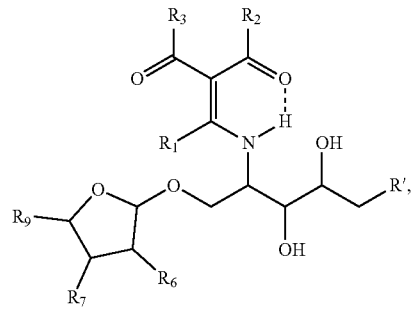

General Formula XIII wherein

R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group, $R_1$ is H, optionally substituted alkyl or optionally substituted aryl, $R_2$ and $R_3$ are independently selected from optionally substituted alkyl, optionally substituted aryl, OR", NHR", NR"R'" wherein R" and R'" are independently H, optionally substituted alkyl or optionally substituted aryl, or wherein $R^2$ and $R^3$ form a cyclic structure characterized by a 5-8-membered ring, $R_6$ is H, OH, $NH_2$, $N_3$, NH-acyl or a carbohydrate moiety, $R_7$ is H, OH or a carbohydrate moiety, $R_9$ is H, $CH_3$, COOH, $CH_2OH$ or a $CH_2O$-carbohydrate moiety, and the dashed line ----- represents a hydrogen bond.

(12) Compound of General Formula XIV, especially obtainable by steps (a) to (c) of the method of claim 1:

General Formula XIV

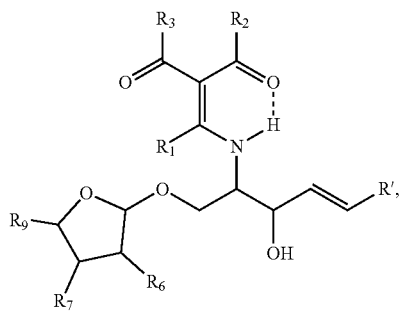

wherein

R', $R_1$, $R_2$, $R_3$, $R_6$, $R_7$ and $R_9$ are as defined in claim 11, and the dashed line ----- represents a hydrogen bond.

(13) Compound of General Formula XV, especially obtainable by steps (a) to (c) of the method of claim 1:

General Formula XV

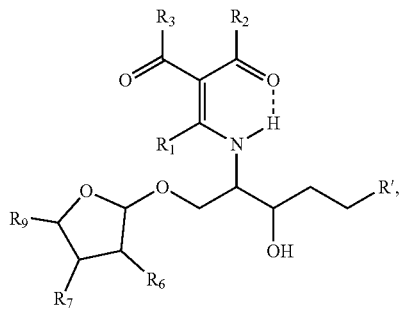

wherein

R', $R_1$, $R_2$, $R_3$, $R_6$, $R_7$ and $R_9$ are as defined in (11), and the dashed line ----- represents a hydrogen bond.

(14) Compound of General Formula XVI, especially obtainable by steps (a) to (c) of the method of claim 1:

General Formula XVI

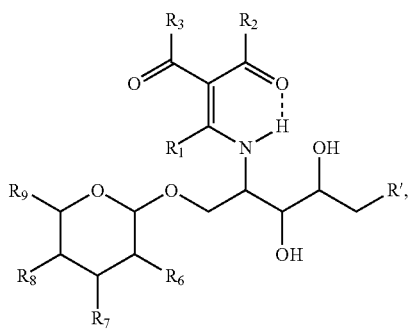

wherein

R', $R_1$, $R_2$, $R_3$, $R_6$ and $R_9$ are as defined in (11), $R_7$ and $R_8$ are independently selected from H, OH and a carbohydrate moiety, and the dashed line ----- represents a hydrogen bond.

(15) Compound of General Formula XVII, especially obtainable by steps (a) to (c) of the method of claim 1:

General Formula XVII

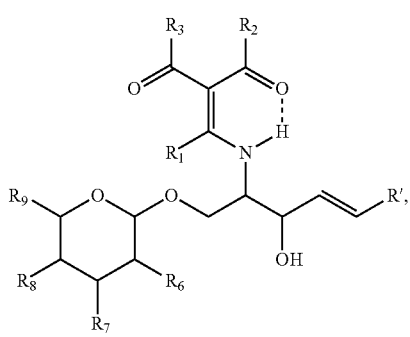

wherein

R', $R_1$, $R_2$, $R_3$, $R_6$ and $R_9$ are as defined in (11), $R_7$ and $R_8$ are as defined in (14), and the dashed line ----- represents a hydrogen bond.

(16) Compound of General Formula XVIII, especially obtainable by steps (a) to (c) of the method of claim 1:

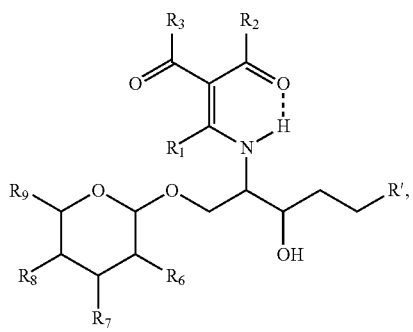

General Formula XVIII wherein

R', $R_1$, $R_2$, $R_3$, $R_6$ and $R_9$ are as defined in (11), $R_7$ and $R_8$ are as defined in (14), and the dashed line ----- represents a hydrogen bond.

(17) Use of a compound of any one of General Formulae IV to XVIII, obtainable by the method of the present invention, for cosmetic, nutritional and/or pharmaceutical applications.

(18) Use of a glycosylated sphingoid base of any one of General Formula XIX to XXIV, obtainable by the method of the present invention, for the production of 1-O-glycosyl-ceramide, 1-O-glycosyl-phytoceramide or 1-O-glycosyl-dihydroceramide, wherein General Formulae XIX to XXIV are as follows:

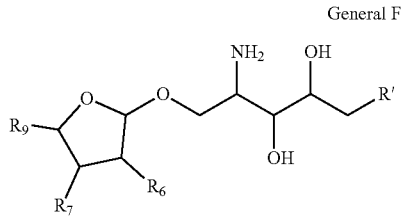

General Formula XIX

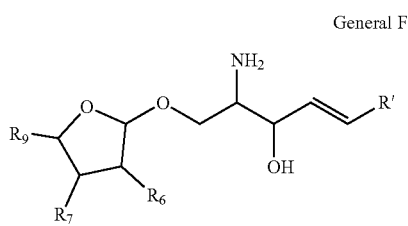

General Formula XX

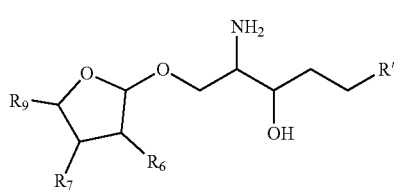

General Formula XXI

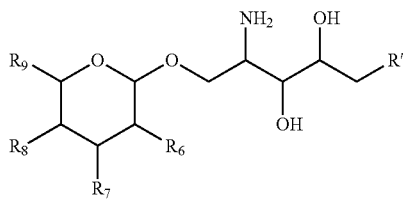

General Formula XXII

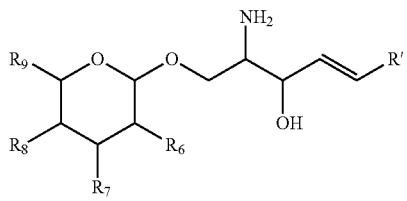

General Formula XXIII

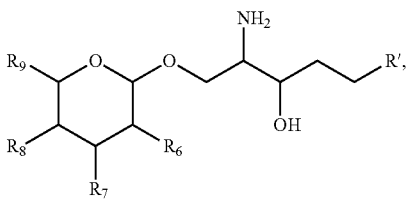

General Formula XXIV wherein

R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group, $R_6$ is H, OH, $NH_2$, $N_3$, NH-acyl or a carbohydrate moiety, $R_7$ and $R_8$ are independently selected from H, OH and a carbohydrate moiety, $R_9$ is H, $CH_3$, COOH, $CH_2OH$ or a $CH_2O$-carbohydrate moiety, and the dashed line ----- represents a hydrogen bond.

The present invention provides N-vinylogous amide-type acceptor molecules in chemical glycosylation reactions where the NH proton is locked into an extremely strong intramolecular hydrogen bond made with one of the carbonyls of the protecting group itself. Thus, the nucleophilicity of the 1-O functionality is not reduced and high yielding glycosylations can be achieved. Additionally, the introduction and removal of vinylogous amide protecting groups lead to quantitative reactions often characterized by great crystalline products/intermediates.

DETAILED DESCRIPTION

The present invention provides a novel economically attractive process for the production of a glycosylated sphingoid base, particularly 1-O-glycosyl-D-erthyro-sphingosine (1-O-glycosyl-(2S,3R,4E)-2-aminooctadec-4-ene-1,3-diol), 1-O-glycosylphytosphingosine (1-O-glycosyl-(2S,3S,4R)-2-amino-1,3,4-octadecanetriol), 1-O-glycosyl-dihydrosphingosine (1-O-glycosyl-(2S,3R)-2-amino-1,3-octadecanediol) or 1-O-glycosyl-(2S,3S,6R)-2-amino-1,3,6-octadecanetriol), suitable for commercial or industrial applications.

In the present specification, the following features are given a definition that should be taken into consideration with the claims and the present detailed description.

The term "optionally substituted" refers to a chemical group that may either carry a substituent or may be unsubstituted.

The term "substituted" means that the group in question is substituted with a group which typically modifies the general chemical characteristics of the group in question. Preferred substituents include but are not limited to halogen, nitro, amino, azido, oxo, hydroxyl, thiol, carboxy, carboxy ester, carboxamide, alkylamino, alkyldithio, alkylthio, alkoxy, acylamido, acyloxy, or acylthio, each of 1 to 6 carbon atoms, preferably of 1 to 3 carbon atoms. The substituents can be used to modify characteristics of the molecule as a whole such as molecule stability, molecule solubility and an ability of the molecule to form crystals. The person skilled in the art will be aware of other suitable substituents of a similar size and charge characteristics, which could be used as alternatives in a given situation.

In connection with the term "alkyl", the term "optionally substituted" (or "substituted") means that the group in question may be (is) substituted one or several times, preferably 1 to 3 times, with group(s) selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo, $C_{1-6}$-alkoxycarbonyl, $C_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkyl-sulphonyl-amino, arylsulphonyl-amino, heteroaryl-sulphonyl-amino, $C_{1-6}$-alkanoyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio, halogen, where any alkyl, alkoxy, and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkyl-carbonylamino, halogen, $C_{1-6}$-alkylthio, $C_{1-6}$-alkyl-sulphonyl-amino, or guanidino.

The term "leaving group" means a group capable of being displaced by a nucleophile in a glycosylation chemical reaction which can promote glycoside formation independently from the applied direct/indirect activation methods. Common leaving groups include halides, thioglycosides, trichloroacetimidates, pentenyl glycosides, beta-O-acetates, etc. known by the person skilled in the art.

The term "derivative" as used in the present application refers to a modified form of a compound, having one or more substituents. Especially in relation to a "sphingoid base" or a "glycosylated sphingoid base", a derivative includes, but is not limited to, forms of a (glycosylated) sphingoid base that have been modified to contain an N-protecting group on an aminoalcohol molecular scaffold, wherein the N-protecting group typically is a vinylogous amide (also termed as "vinylogous amide derivative").

In the context of the present invention, the terms "sphingosine" and "D-erythro-sphingosine" are used interchangeably.

In the context of the present invention, the terms "DL-erythro-Dihydrosphingosine" and "dihydrosphingosine" are used interchangeably.

In the context of the present invention, the terms "D-ribo-phytosphingosine" and "phytosphingosine" are used interchangeably.

The term "a" grammatically is a singular, but it may as well mean the plural of e.g. the intended compound or sphingoid base. For example, the skilled person would understand that in the expression "the production of a sphingoid base", the production of not only one single sphingoid base, but of many sphingoid bases of the same type are meant.

The term "carbohydrate moiety" (also referred to as glycosyl moiety) is when used herein defined broadly to encompass (but not being limited to) derivatized and underivatized mono-, di- and oligosaccharide-containing groups capable of making either an alpha- or a beta-glycosidic linkage.

A carbohydrate moiety may represent a linear or branched structure comprising 1 to 16 monosaccharide units. Some of the more abundantly used monosaccharide units include glucose, N-acetyl-glucosamine, mannose, galactose, N-acetyl-neuraminic acid, N-acetyl-galactosamine, fucose, glucuronic acid, galacturonic acid, etc. The skilled person will understand that an "O-carbohydrate moiety" is a carbohydrate moiety that is linked to an oxygen group of another molecule.

In a first aspect, the present invention relates to a method for producing a glycosylated sphingoid base, or a salt thereof, starting from a sphingoid base of General Formula I, II or III, wherein the sphingoid base has a vinylogous amide-type N-protecting group:

General Formula I

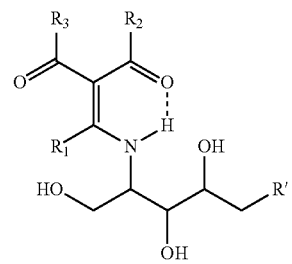

General Formula II

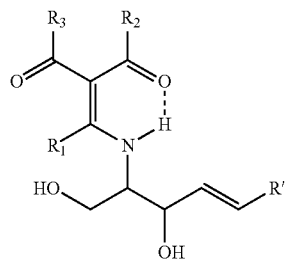

-continued

General Formula III

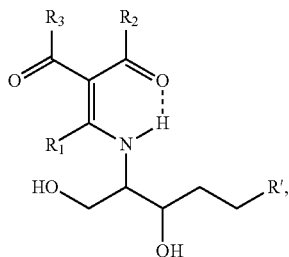

wherein

R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group, $R_1$ is H, optionally substituted alkyl or optionally substituted aryl, $R_2$ and $R_3$ are independently selected from optionally substituted alkyl, optionally substituted aryl, OR", NHR", NR"R'" wherein R" and R'" are independently H, optionally substituted alkyl or optionally substituted aryl, or wherein $R^2$ and $R^3$ form a cyclic structure characterized by a 5-8-membered ring, and the dashed line ----- represents a hydrogen bond, this method comprising the steps of:

a) Protecting the hydroxyl (OH) groups at $C_3$ and $C_4$ of General Formula I or at $C_3$ of General Formula II or III, respectively, with an O-protecting group to form a compound of General Formula IV (where General Formula I is the precursor or starting compound), General Formula V (where General Formula II is the precursor or starting compound) or General Formula VI (where General Formula III is the precursor or starting compound):

General Formula IV

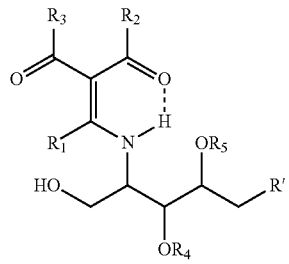

General Formula V

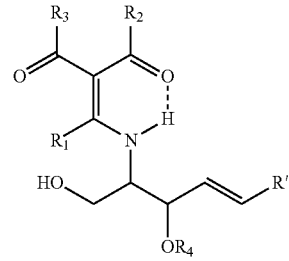

General Formula VI

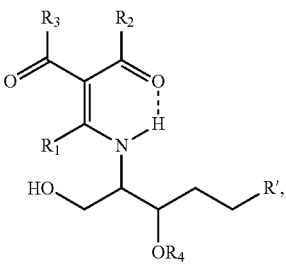

wherein

R', $R_1$, $R_2$ and $R_3$ are as defined above, $R_4$ and $R_5$ are independently selected from acyl, optionally substituted alkyl, optionally substituted acetal, optionally substituted ketal or silyl or wherein $R_4$ and $R_5$ form a cyclic structure (possible for a compound of General Formula IV) and the dashed line ----- represents a hydrogen bond, b) Reacting a compound of General Formula IV, V or VI as an acceptor molecule with a carbohydrate donor, wherein the carbohydrate donor comprises an optionally substituted furanose or an optionally substituted pyranose ring, to form a compound of General Formula VII, VIII, IX, X, XI or XII, wherein the optionally substituted furanose ring or the optionally substituted pyranose ring is covalently linked via either an alpha- or a beta-glycosidic linkage to the $C_1$—O group of the acceptor molecule:

General Formula VII

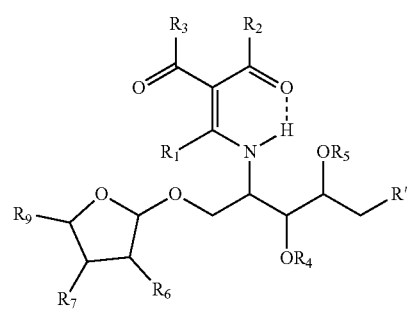

General Formula VIII

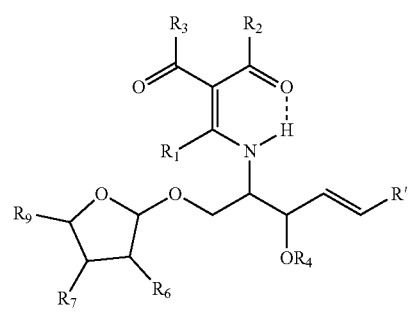

-continued

General Formula IX

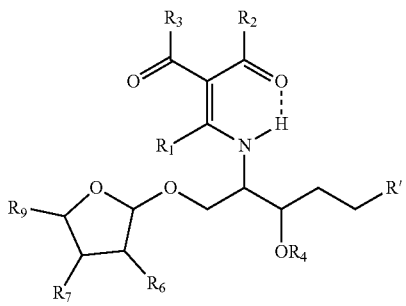

General Formula X

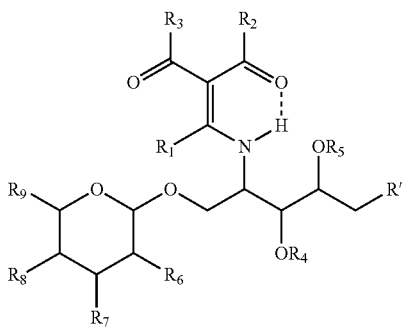

General Formula XI

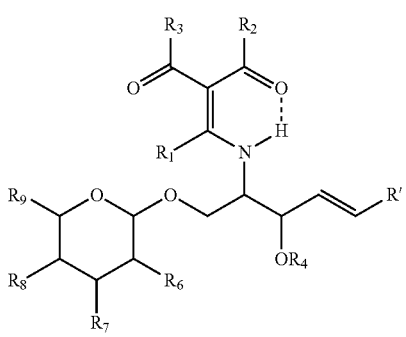

General Formula XII

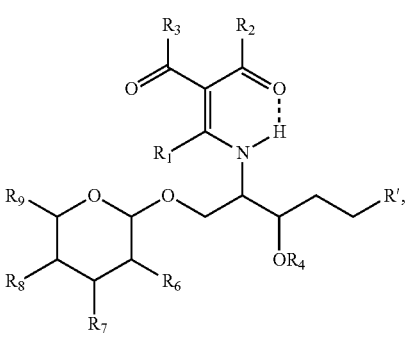

wherein

R', $R_1$, $R_2$, $R_3$, $R_4$ and $R_5$ are as defined above, $R_6$ is O-acyl, $N_3$, NH-acyl, optionally substituted O-alkyl, O-carbohydrate moiety, O-silyl, optionally substituted acetal or optionally substituted ketal, $R_7$ and $R_8$ are independently selected from O-acyl, optionally substituted acetal, optionally substituted ketal, O-silyl, optionally substituted O-alkyl or an O-carbohydrate moiety, $R_9$ is H, $CH_3$, COOH, COOR'''' (where R'''' is optionally substituted alkyl) or $CH_2OR^V$, where $R^V$ is selected from acyl, optionally substituted alkyl, optionally substituted acetal, optionally substituted ketal, silyl or a carbohydrate moiety, and the dashed line ---- represents a hydrogen bond, c) Removing the O-protecting group or O-protecting groups present on a compound of General Formula VII, VIII, IX, X, XI or XII to form a compound of General Formula XIII, XIV, XV, XVI, XVII or XVIII, respectively:

General Formula XIII

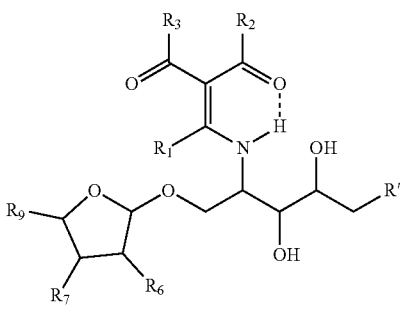

General Formula XIV

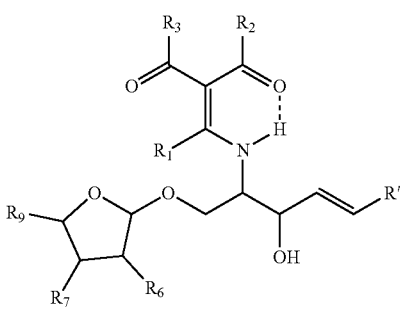

General Formula XV

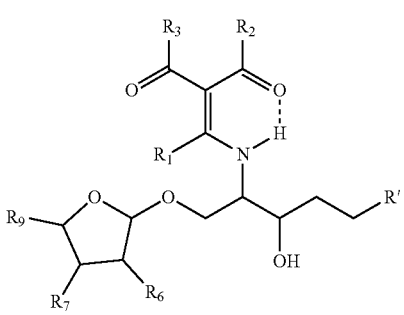

General Formula XVI

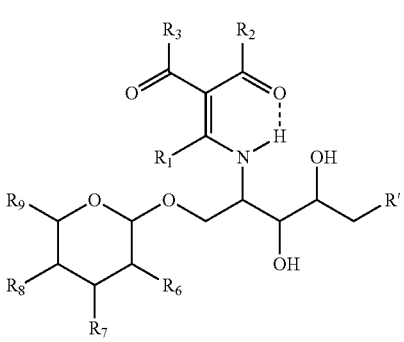

General Formula XVII

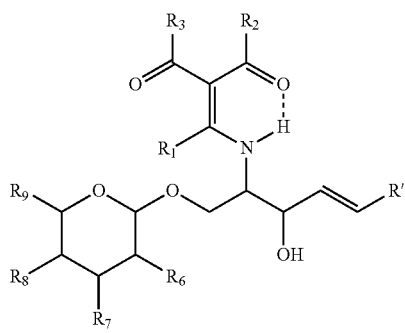

General Formula XVIII

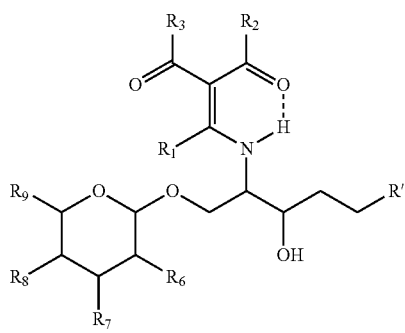

wherein R', $R_1$, $R_2$ and $R_3$ are as defined above, $R_6$ is H, OH, $NH_2$, $N_3$, NH-acyl or a carbohydrate moiety, $R_7$ and $R_8$ are independently selected from H, OH and a carbohydrate moiety, $R_9$ is H, $CH_3$, COOH, $CH_2OH$ or a $CH_2O$-carbohydrate moiety, and the dashed line ----- represents a hydrogen bond, d) Removing the N-protecting group or N-protecting groups present on a compound of General Formula XIII, XIV, XV, XVI, XVII or XVIII to form a compound of General Formula XIX, XX, XXI, XXII, XXIII or XXIV, respectively, or a salt thereof:

General Formula XIX

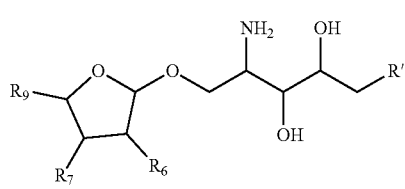

General Formula XX

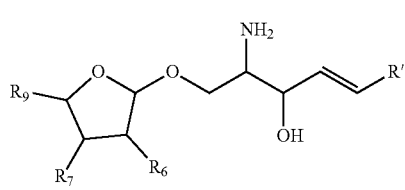

General Formula XXI

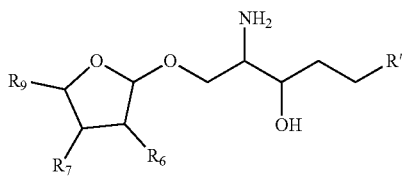

General Formula XXII

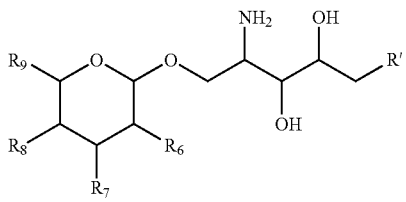

General Formula XXIII

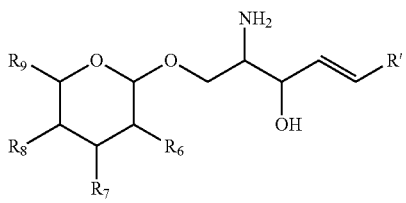

General Formula XXIV

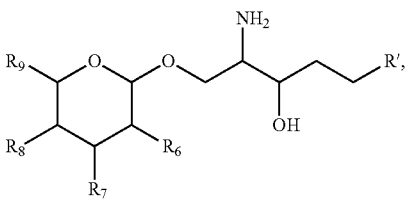

wherein

R', is as defined above, $R_6$ is H, OH, $NH_2$, $N_3$, NH-acyl or a carbohydrate moiety, $R_7$ and $R_8$ are independently selected from H, OH and a carbohydrate moiety, $R_9$ is H, $CH_3$, COOH, $CH_2OH$ or a $CH_2O$-carbohydrate moiety, and the dashed line ----- represents a hydrogen bond.

The skilled person will be aware that position $C_1$, $C_2$, $C_3$, $C_4$ and $C_5$ refer to the carbon atoms of the sphingoid base of General Formula II, even if substituents would strictly taken change the exact positions of the carbon atoms. In other words, when speaking of $C_1$, $C_2$, $C_3$, $C_4$ and $C_5$, reference is herein always made to the respective carbon atoms of the sphingoid base of General Formula II.

The skilled person will understand that the compounds of General Formulae XIX, XX, XXI, XXII, XXIII or XXIV that are formed in step (d) of the method of the present invention are the glycosylated sphingoid bases to be produced with the method.

The skilled person will understand that the starting compounds of General Formulae I, II and III, respectively, define the possible General Formulae of the following steps of the method of the present invention. If e.g. a compound of General Formula I is used as a starting compound for the method, a compound of General Formula IV (and not a compound of General Formula V or VI) will be formed in step (a) of the method of the present invention. The same applies to the steps to follow. On top of that subdivision, the choice of the carbohydrate donor in step (b) of the method of the present invention further defines the possible General Formulae of the method steps to follow. If e.g. a carbohydrate donor comprising an optionally substituted furanose ring is used in step (b) of the method of the present invention, a compound of General Formulae VII, VIII and IX, respectively (depending on the starting compound used), and not a compound of General Formulae X, XI or XII, will be formed.

The General Formulae that are be mentioned in the following methods below are not illustrated again. A skilled person will be aware, however, that the General Formulae and the defined rests (R) as defined above in detail will also apply to the coming methods.

Accordingly, one embodiment of the first aspect of the present invention relates to a method for producing a glycosylated sphingoid base, or a salt thereof, starting from an N-protected sphingoid base of General Formula I, wherein the N-protected sphingoid base has a vinylogous amide as an N-protecting group, this method comprising the steps of:

(a) Protecting the hydroxyl (OH) groups at $C_3$ and $C_4$ of General Formula I with an O-protecting group to form a compound of General Formula IV, (b) Reacting a compound of General Formula IV as an acceptor molecule with a carbohydrate donor, wherein the carbohydrate donor comprises an optionally substituted furanose or an optionally substituted pyranose ring,
to form a compound of General Formula VII or X, respectively,
wherein the optionally substituted furanose ring or the optionally substituted pyranose ring is covalently linked via either an alpha- or a beta-glycosidic linkage to the $C_1$—O group of the acceptor molecule, (c) Removing O-protecting groups present on the compound of General Formula VII or X to form a compound of General Formula XIII or XVI, respectively, (d) Removing the N-protecting group or N-protecting groups present on the compound of General Formula XIII or XVI to form a compound of General Formula XIX or XXII, respectively.

Another embodiment of the first aspect of the present invention relates to a method for producing a glycosylated sphingoid base, or a salt thereof,
starting from an N-protected sphingoid base of General Formula II, wherein the N-protected sphingoid base has a vinylogous amide as an N-protecting group, this method comprising the steps of:

(a) Protecting the hydroxyl (OH) group at $C_3$ of General Formula II with an O-protecting group to form a compound of General Formula V, (b) Reacting a compound of General Formula V as an acceptor molecule with a carbohydrate donor, wherein the carbohydrate donor comprises an optionally substituted furanose or an optionally substituted pyranose ring, to form a compound of General Formula VIII or XI, respectively, wherein the optionally substituted furanose ring or the optionally substituted pyranose ring is covalently linked via either an alpha- or a beta-glycosidic linkage to the $C_1$—O group of the acceptor molecule, (c) Removing the O-protecting group or O-protecting groups present on a compound of General Formula VIII or XI to form a compound of General Formula XIV or XVII, respectively, (d) Removing the N-protecting group or N-protecting groups present on a compound of General Formula XIV or XVII to form a compound of General Formula XX or XXIII, respectively.

Yet another embodiment of the first aspect of the present invention relates to a method for producing a glycosylated sphingoid base, or a salt thereof, starting from an N-protected sphingoid base of General Formula III, wherein the N-protected sphingoid base has a vinylogous amide as an N-protecting group, this method comprising the steps of:

(a) Protecting the hydroxyl (OH) group at $C_3$ of General Formula III with an O-protecting group to form a compound of General Formula VI, Reacting a compound of General Formula VI as an acceptor molecule with a carbohydrate donor, wherein the carbohydrate donor comprises an optionally substituted furanose or an optionally substituted pyranose ring,
to form a compound of General Formula IX or XII, respectively,
wherein the optionally substituted furanose ring or the optionally substituted pyranose ring is covalently linked via either an alpha- or a beta-glycosidic linkage to the $C_1$—O group of the acceptor molecule, (b) Removing the O-protecting group or O-protecting groups present on a compound of General Formula IX or XII to form a compound of General Formula XV or XVIII, respectively, (c) Removing the N-protecting group or O-protecting groups present on a compound of General Formula XV or XVIII to form a compound of General Formula XXI or XXIV, respectively, or a salt thereof.

The method of the first aspect of the present invention provides compounds of General Formulae XIX to XXIV, which are glycosylated sphingoid bases, or salts of those compounds of General Formulae XIX to XXIV or glycosylated sphingoid bases. The salts are preferably pharmaceutically acceptable salts or other generally acceptable salts, unless they would be excluded for chemical reasons, which the skilled person will readily understand.

The N-protected sphingoid bases of General Formula I, II or III, which are used as starting compounds for the method according to the present invention, are vinylogous amides and are typically produced by protecting the $NH_2$ (amino) group of a compound of General Formula Ia, IIa or IIIa, respectively, with an N-protecting group by addition of an N-protecting group reagent to the compound of General Formula Ia, IIa or IIIa. The N-protecting group is a vinylogous amide-type N-protecting group suitable to form vinylogous amides. The N-protecting group reagent is a vinylogous reagent and may be a vinylogous acid, a vinylogous ester, a vinylogous amide or a vinylogous acid halide.

General Formula Ia

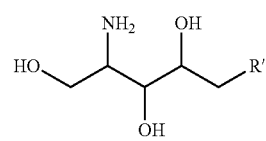

General Formula IIa

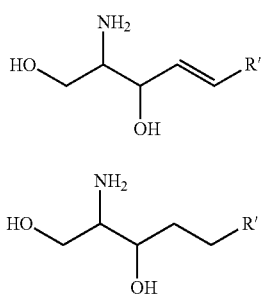

General Formula IIIa

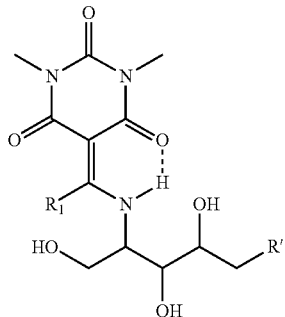

Preferably, the vinylogous reagent is an N,N-disubstituted vinylogous amide reagent, more preferably an N,N-dialkyl-barbituric acid-derived reagent. Even more preferably, the vinylogous reagent is 1,3-dimethyl-5-[(dimethylamino)methylene]-2,4,6(1H,3H,5H)-trioxopyrimidine (DTPM-reagent) (CAS: 35824-98-7; $C_9H_{13}N_3O_3$).

When DTPM-reagent is used as the vinylogous reagent, a compound of General Formula Ib, IIb and IIIb, respectively, is formed. The skilled person will understand that all the subsequent General Formulae formed in the method of the present invention will in that case equally carry DTPM as protecting group (except General Formulae XVIV to XXIV, for which the N-protecting group has been removed).

General Formula Ib

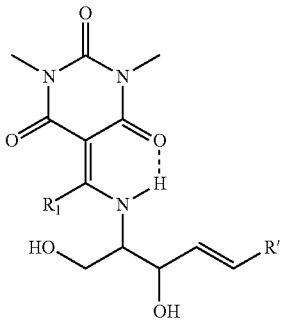

General Formula IIb

General Formula IIIb

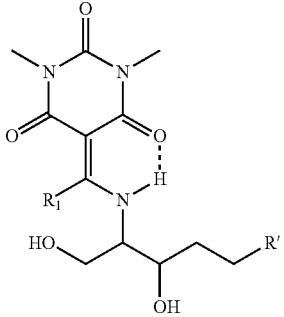

The vinylogous reagent preferably has a cyclic structure providing a robust stability and crystalline properties. The preparation of vinylogous reagents are described in publications *Tetrahedron Letters*, 2001, 42, 3129-3132; WO 98/38197. For the preparation, the compound according to General Formula II and the vinylogous reagent may be mixed in water, organic solvents or in their aqueous mixtures. The reactions may optionally be catalyzed with organic or inorganic bases at temperatures ranges from 0-150° C., preferably at temperatures ranging from 20-120° C. More preferably, the reaction goes to completion at ambient temperature. The reactions are preferably carried out in organic solvents at room temperature (r.t.) or between 40-100° C. A person skilled in art has the knowledge to conduct, isolate and purify the novel compounds by using standard methods of synthetic organic chemistry.

DTPM protection of carbohydrates and primary amines are well documented and their preparation are known for the person skilled in Art (*Tetrahedron Letters*, 2001, 42, 3129-3132).

Preferably, the introduction of DTPM protecting group may be performed using the DTPM-reagent dissolved in $H_2O$ or in organic solvents, such as methanol and $CH_2Cl_2$. The reaction does not require extreme conditions and affords high conversion. The DTPM-protected compounds of General Formula Ib, IIb and IIIb may be precipitated directly from the reaction mixtures.

Example 1 (see below under "Examples") provides one representative experimental example of the described DTPM-protection.

The N-protection step may in one embodiment be included as a method step of the method of the present invention.

In a preferred embodiment, the stereochemistry of a compound of General Formula I (or of General Formula Ib) and accordingly of a compound of the General Formulae of the subsequent steps of the method of the first aspect of the present invention, corresponds to the stereochemistry of phytosphingosine. Likewise, in a preferred embodiment, the stereochemistry of a compound of General Formula II (or of General Formula lib) and accordingly of a compound of the General Formulae of the subsequent steps of the method of the first aspect of the present invention, corresponds to the stereochemistry of D-erythro-sphingosine. Likewise, in another preferred embodiment, the stereochemistry of a compound of General Formula III (or of General Formula Mb) and accordingly of a compound of the General Formulae of the subsequent steps of the method of the first aspect of the present invention corresponds to the stereochemistry of dihydrosphingosine. In other words, the stereochemical configuration of the compounds of General Formulae I, IV, VII, X, XIII, XVI, XIX and XXII (or their preferred versions wherein the N-protecting group is DTPM) preferably equals the stereochemical configuration of phytosphingosine (2S, 3S,4R), the stereochemical configuration of the compounds of General Formulae II, V, VIII, XI, XIV, XVII, XX, and XXIII (or their preferred versions wherein the N-protecting group is DTPM) preferably equals the stereochemical configuration of D-erythro-sphingosine (2S,3R,4E) and the stereochemical configuration of the compounds of General Formulae III, VI, IX, XII, XV, XVIII, XXI and XXIV preferably equals the stereochemical configuration of dihydrosphingosine (2S,3R).

In the following, when reference is made to the General Formulae, their preferred versions, wherein the N-protecting group is DTPM and/or the stereochemical configuration equals the one of phytosphingosine, D-erythro-sphingosine or dihydrosphingosine, and all coming preferred versions, may be also addressed (and more preferred then).

In a more preferred embodiment, R' of General Formulae I to XXIV is an alkyl chain having 13 carbon atoms. Even more preferably, R' of General Formulae I to XXIV is $C_{13}H_{27}$ or $CH(OH)C_{12}H_{25}$, especially —$C_{13}H_{27}$ or —$CH(OH)C_{12}H_{25}$.

In step (a) of the method of the present invention, the hydroxyl groups at $C_3$ and $C_4$ of General Formula I or at $C_3$ of General Formula II or III, respectively, are protected with an O-protecting group by addition of an O-protecting group reagent.

The O-protecting groups at $C_3$ and $C_4$ may be the same or different and are selected from acyl, optionally substituted alkyl, optionally substituted acetal, optionally substituted ketal or silyl or one O-protecting group may form one cyclic structure with the hydroxyl groups of both $C_3$ and $C_4$ (possible for a compound of General Formula IV). The O-protecting group at $C_3$ and $C_4$ is preferably acyl. The O-protecting group forming the cyclic structure with the hydroxyl groups of both $C_3$ and $C_4$ preferably may be an optionally substituted cyclic carbonate, an optionally substituted cyclic acetal or an optionally substituted cyclic ketal, more preferably an optionally substituted cyclic acetal or an optionally substituted cyclic ketal. Especially, the optionally substituted cyclic acetal is an optionally substituted benzylidene and the optionally substituted cyclic ketal is an optionally substituted isopropylidene.

The introduction of an O-protecting group used is a well-known process for a person skilled in art by reacting N-protected sphingoid bases with activated acid, activated alkyl, activated silyl, activated aldehyde or activated ketal reagents in the presence of base or acid catalyst. The use of tertiary amine organic bases, Fewis acids and protic acid catalysts are preferred. For example, 3,4-diols of a compounds characterized by General Formula I with aldehyde, ketone, acyclic dialkylacetals or acyclic dialkylketal, preferably dimethyl acetal and dimethyl ketal, reagents in the presence of protic acid or Fewis acid catalysts in organic solvents.

Example 2 (see below under "Examples") provides one representative experimental example for step (a) of the method of the present invention.

It is noted that N-vinylogous amide protection alone might in some cases be sufficient—without hydroxyl group protection—for the glycosylation step (b) of the method of the present invention. Accordingly, in one embodiment, step (a) of the method is an optional step.

In step (b) of the method of the present invention, a compound of General Formula IV, V or VI as an acceptor molecule is reacted with a carbohydrate (glycosyl) donor, wherein the carbohydrate donor comprises an optionally substituted furanose or an optionally substituted pyranose ring, to form a compound of General Formula VII, VIII, IX, X, XI or XII, wherein the optionally substituted furanose ring or the optionally substituted pyranose ring is covalently linked via either an alpha- or a beta-glycosidic linkage to the $C_1$—O group of the acceptor molecule. The optionally substituted furanose or the optionally substituted pyranose ring of a carbohydrate donor typically comprises a direct or an indirect leaving group at an anomeric position for a glycosylation reaction to take place. Accordingly, the optionally furanose or the optionally substituted pyranose ring preferably comprises a direct or an indirect leaving group suitable for a glycosylation reaction or at an anomeric position.

Glycosyl donors may be monosaccharide or oligosaccharide derivatives which carry a leaving group at an anomeric position. O- and N-nucleophiles present on the glycosyl donor molecules are usually blocked by O- and/or N-protecting groups facilitating a selective glycosylation reaction with the vinylogous amide sphingoid base acceptors. Accordingly, the glycosyl donor and especially the optionally substituted furanose or the optionally substituted pyranose ring of step (b) of the method of the present invention preferably carry one or several O- and/or N-protecting group(s). The skilled person will be aware of O- and N-protecting groups typically used. Typical donor molecules are halogen sugars, thioglycosides, beta-1-O-acylated sugars, 1-O-trichloroacetimidates, carbohydrate oxazolines, pentenyl glycosides, etc. known by the person skilled in the art.

Preferred glycosyl donors include halogen sugars, thioglycosides, beta-1-O-acylated sugars and 1-O-trichloroacetimidates carrying carbohydrate moieties found in naturally occurring glycosphingolipids, more preferably carbohydrate moieties found in human skin, in human milk, and in human brain glycosphingolipids, even more preferably carbohydrate moieties found in the ganglio-series of glycosphingolipids.

The solvent used for glycosylation can be selected from dichloromethane, toluene, tetrahydrofuran, acetonitrile, DMF, etc. or their mixtures. The reaction can be performed at temperatures ranging from −20° C. to 50° C. depending on donor/acceptor reactivities and the types of glycosylation reactions.

Promoters such as non-nucleophilic acids, Lewis acids, thiophilic promoters, alkylating agents, etc. such as triflic acid, TMS-triflate, $BF_3xEt_2O$, NBS, NIS, DMTST, etc. can be used according to the types of activations.

Donor—acceptor pairs, promoters, solvents, temperatures, reaction times are known by a person skilled in the glycosylation art.

Example 3 (see below under "Examples") provides one representative experimental example for step (b) of the method of the present invention.

In step (c) of the method of the present invention, the O-protecting group(s) is/are removed from a compound of General Formula VII, VIII, IX, X, XI or XII to form a compound of General Formula XIII, XIV, XV, XVI, XVII or XVIII, respectively.

At least one O-protecting group is present on the acceptor molecule (sphingoid base) moiety of the compound (where they were introduced in step (a) of the present invention) and at least one further O-protecting group may as well be present on the glycosyl donor moiety of the compound.

The removal of the O-protecting group(s) on the acceptor molecule moiety may be performed independently from (especially when different types of O-protecting groups are present) or jointly with the removal of the O-protecting group(s) found on the glycosyl donor moiety.

Step (c) of the method of the present invention refers to the removal of the O-protecting group(s) introduced in step (b) of the method of the present invention, as well as of the O-protecting group(s) present on the glycosyl donor moiety of the compound.

The O-protecting group(s) removal, even when multiple types of O-protecting groups are present, is a well-known procedure for the skilled person.

Example 4 (see below under "Examples") provides one representative experimental example for step (c) of the method of the present invention.

In step (d) of the method of the present invention, the N-protecting group(s) is/are removed from a compound of General Formula XIII, XIV, XV, XVI, XVII or XVIII to form a compound of General Formula XIX, XX, XXI, XXII, XXIII or XXIV, respectively, or a salt thereof.

One N-protecting group is present on the sphingoid base moiety of the compound and at least one further N-protecting group may as well be present on the glycosyl donor moiety of the compound.

The removal of the N-protecting groups may be performed independently from one another (especially when different types of N-protecting groups are present) or jointly.

Step (d) of the method of the present invention refers to the removal of the N-protecting group being the vinylogous amide-type protecting group on the sphingoid base moiety of the compound as well as of the N-protecting group(s) present on the glycosyl donor moiety of the compound.

The reagent used for this step may be selected from an aqueous inorganic base, $NH_3$, primary amines, hydrazine, hydrazine derivatives, hydroxylamine and hydroxylamine derivatives.

The reaction may be performed in an organic solvent such as dichlormethane, acetonitrile, methanol, tetrahydrofuran or toluene with or without subsequent salt formation. The preferred temperature range for the reaction is from 20 to 120° C.

Protonation of the amino group of the sphingoid bases can be achieved by inorganic and organic acid. Preferably, HCl, HBr, $H_2SO_4$, $HNO_3$, formic acid, acetic acid, citric acid, ascorbic acid, etc. can be used for salt formation. Salt formation on the carbohydrate moiety could also be possible when acidic carbohydrate residues are making ion pairs with monovalent and divalent ions such as ammonium, $Na^+$, $K^+$, $Ca^{2+}$, $Mg^{2+}$, etc. Details of salt formations of suitable for the preparation of 1-O-glycosyl-sphingoid bases is known by the person skilled in the art.

Example 5 (see below under "Examples") provides one representative experimental example for step (d) of the method of the present invention.

Steps (a) to (d) of the method of the present invention are performed in the order mentioned, i.e. beginning with step (a), continuing with step (b) and (c), and ending with step (d). The method of the present invention may as well comprise further steps in addition to steps (a) to (d), provided they do not negatively affect the reactions of steps (a) to (f), which the skilled person will easily determine. For example, as mentioned above, the N-protection step may be included as a method step of the method of the present invention.

In a second aspect, the present invention provides novel compounds of the method according to the present invention, represented by General Formulae IV to XVIII. In one preferred embodiment, the N-protecting group of a compound of General Formula IV to XVIII is DTPM. In another preferred embodiment, the stereochemical configuration of a compound of General Formula IV, VII, X, XIII, XVI, XIX and XXII equals the stereochemical configuration of phytosphingosine (2S,3S,4R), the stereochemical configuration of a compound of General Formula V, VIII, XI, XIV and XVII equals the stereochemical configuration of D-erythro-sphingosine (2S,3R,4E) and the stereochemical configuration of a compound of General Formulae VI, IX, XII, XV and XVIII equals the stereochemical configuration of dihydrosphingosine (2S,3R). In a more preferred embodiment, N-protecting group of a compound of General Formula I to XXIV is DTPM and the stereochemical configuration of a compound of General Formulae IV, VII, X, XIII and XVI equals the stereochemical configuration of phytosphingosine (2S,3S,4R), the stereochemical configuration of a compound of General Formulae V, VIII, XI, XIV and XVII equals the stereochemical configuration of D-eryfhro-sphingosine (2S,3R,4E) and the stereochemical configuration of a compound of General Formulae VI, IX, XII, XV and XVIII equals the stereochemical configuration of dihydrosphingosine (2S, 3R).

In a preferred embodiment, R' of General Formulae IV to XXVIII is an alkyl chain having 13 carbon atoms. Even more preferably, R' of General Formulae IV to XXVIII is $C_{13}H_{27}$ or $CH(OH)C_{12}H_{25}$, especially $—C_{13}H_{27}$ or $—CH(OH)C_{12}H_{25}$.

An inventive compound of the present invention is represented by General Formula IV, V or VI:

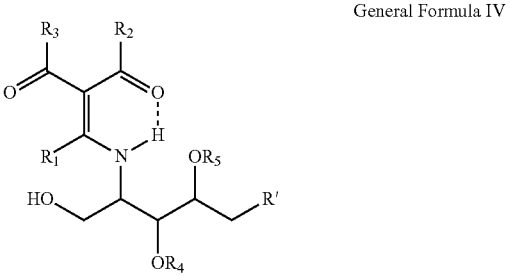

General Formula IV

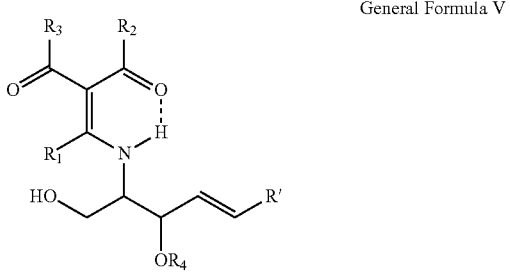

General Formula V

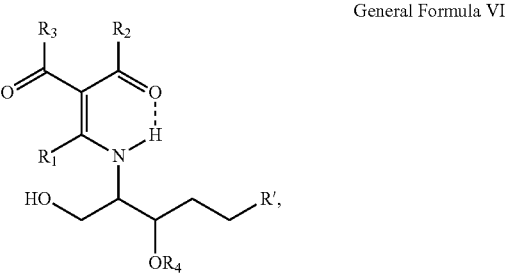

General Formula VI wherein

R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group, $R_1$ is H, optionally substituted alkyl or optionally substituted aryl, $R_2$ and $R_3$ are independently selected from optionally substituted alkyl, optionally substituted aryl, OR", NHR", NR"R'" wherein R" and R'" are independently H, optionally substituted alkyl or optionally substituted aryl, or wherein $R^2$ and $R^3$ form a cyclic structure characterized by a 5-8-membered ring, $R_4$ and $R_5$ are independently selected from acyl, optionally substituted alkyl, optionally substituted acetal, optionally substituted ketal or silyl or wherein $R_4$ and $R_5$ form a cyclic structure (possible for a compound of General Formula IV)

and the dashed line ----- represents a hydrogen bond.

A compound of General Formula IV, V or VI is especially obtainable by step (a) of the method of the present invention.

An inventive compound of the present invention is represented by General Formula VII, VIII, IX, X, XI or XII:

General Formula VII

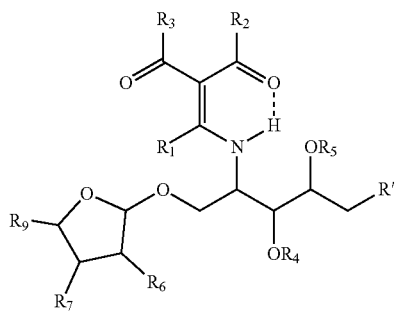

General Formula VIII

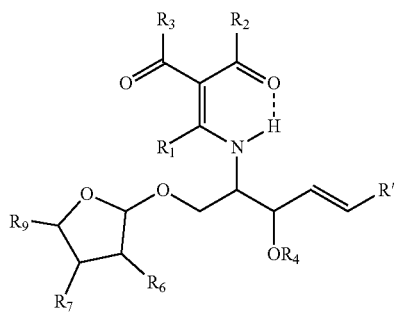

General Formula IX

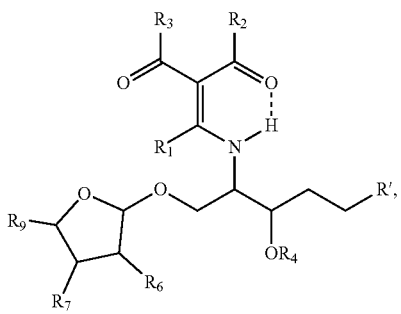

General Formula X

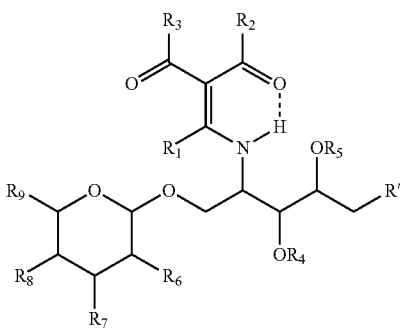

General Formula XI

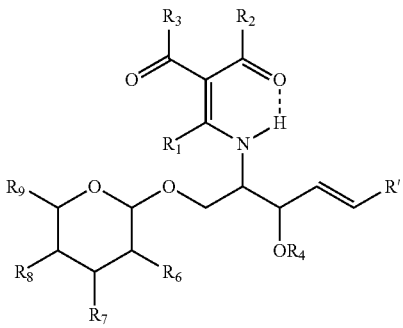

General Formula XII

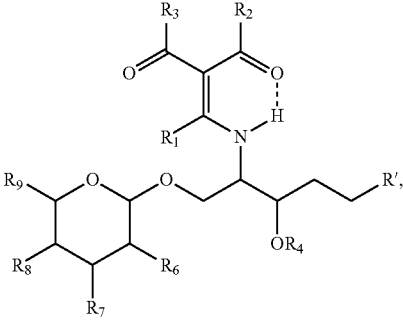

wherein

R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group, $R_1$ is H, optionally substituted alkyl or optionally substituted aryl, $R_2$ and $R_3$ are independently selected from optionally substituted alkyl, optionally substituted aryl, OR", NHR", NR"R'" wherein R" and R'" are independently H, optionally substituted alkyl or optionally substituted aryl, or wherein $R^2$ and $R^3$ form a cyclic structure characterized by a 5-8-membered ring, $R_4$ and $R_5$ are independently selected from acyl, optionally substituted alkyl, optionally substituted acetal, optionally substituted ketal or silyl or wherein $R_4$ and $R_5$ form a cyclic structure (possible for a compound of General Formula VII and X), R₆ is O-acyl, N₃, NH-acyl, optionally substituted O-alkyl, O-carbohydrate moiety, O-silyl, optionally substituted acetal or optionally substituted ketal, R₇ and R₈ are independently selected from O-acyl, optionally substituted acetal, optionally substituted ketal, O-silyl, optionally substituted O-alkyl or an O-carbohydrate moiety, R₉ is H, CH₃, COOH, COOR'''' (where R'''' is optionally substituted alkyl) or CH₂OR$^V$, where R$^V$ is selected from acyl, optionally substituted alkyl, optionally substituted acetal, optionally substituted ketal, silyl or a carbohydrate moiety, and the dashed line ----- represents a hydrogen bond.

A compound of General Formula VII, VIII, IX, X, XI or XII is especially obtainable by steps (a) to (b) of the method of the present invention.

An inventive compound of the present invention is represented by General Formula XIII, XIV, XV, XVI, XVII or XVIII:

General Formula XIII

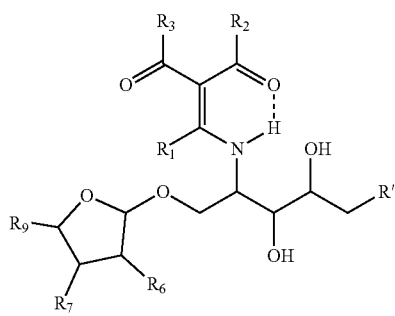

General Formula XIV

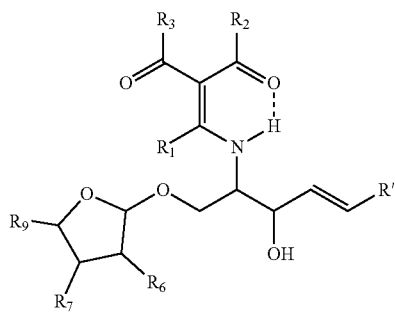

General Formula XV

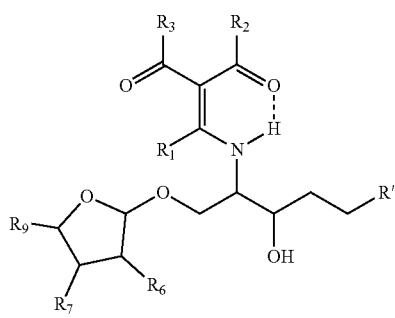

-continued

General Formula XVI

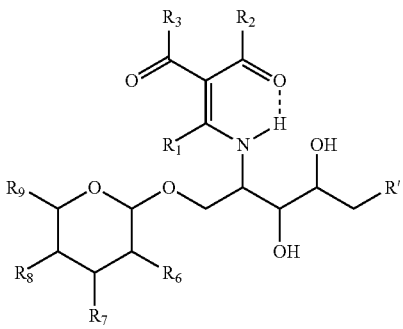

General Formula XVII

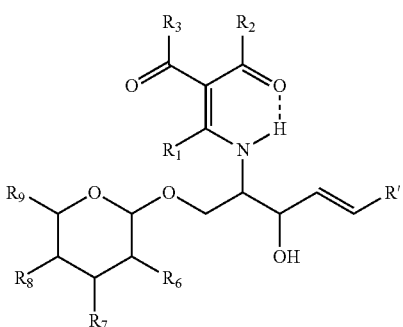

General Formula XVIII

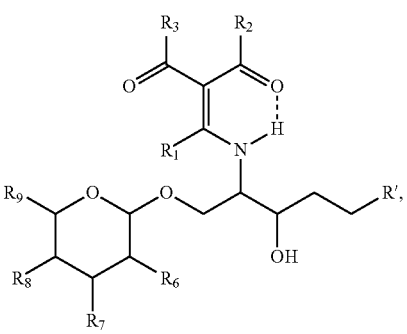

wherein

R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group, R₁ is H, optionally substituted alkyl or optionally substituted aryl, R₂ and R₃ are independently selected from optionally substituted alkyl, optionally substituted aryl, OR", NHR", NR"R'" wherein R" and R'" are independently H, optionally substituted alkyl or optionally substituted aryl, or wherein R² and R³ form a cyclic structure characterized by a 5-8-membered ring, R₆ is H, OH, NH₂, N₃, NH-acyl or a carbohydrate moiety, R₇ and R₈ are independently selected from H, OH and a carbohydrate moiety, $R_9$ is H, $CH_3$, COOH, $CH_2OH$ or a $CH_2O$-carbohydrate moiety, and the dashed line ----- represents a hydrogen bond.

A compound of General Formula XIII, XIV, XV, XVI, XVII or XVIII is especially obtainable by steps (a) to (c) of the method of the present invention.

A third aspect of the invention provides the use of a novel 1-O-glycosylated sphingoid base, being a compound of General Formulae XIX to XXIV, for cosmetic, nutritional and/or pharmaceutical applications.

In one embodiment, a compound of General Formula XIX, XX, XXI, XXII, XXII or XXIV may be used as a pharmaceutical agent and/or for the preparation of a pharmaceutical composition. The compound used may be obtained by the method according to the present invention.

In another embodiment, a compound of General Formula XIX, XX, XXI, XXII, XXII or XXIV may be used for the preparation of a nutritional formulation, e.g. a food supplement. The compound used may be obtained by the method according to the present invention.

In yet another embodiment, a compound of General Formula XIX, XX, XXI, XXII, XXII or XXIV may be used for the preparation of a cosmetic product.

A fourth aspect of the invention provides the use of a novel 1-O-glycosylated sphingoid base, being a compound of General Formulae XIX to XXIV, for the production of 1-O-glycosyl-ceramides, 1-O-glycosyl-phytoceramides or 1-O-glycosyl-dihydroceramides, especially via N-acylation.

The N-acylation may be performed using an acyl moiety of a $C_{12}$-$C_{30}$ acyl group which can be saturated, unsaturated or optionally substituted. The acylation may be performed by both lipase-assisted biocatalysis or chemistry via the use of the corresponding carboxylic acid, acid chloride, ester or anhydride in the presence of a base, preferably in the presence of an organic base, more preferably in the presence of pyridine, triethylamine (TEA) or diisopropylethylamine (DIPEA).

EXAMPLES

Example 1

Preparation of (2S,3S,4R)-2-((1,3-dimethyl-2,4,6 (1H,3H,5H)-trioxopyrimidine-5-ylidene)methyl)-octadecan-1,3,4-triol Phytosphingosine (4.8 g, 15.1 mmol) is added to methanol (150 mL) at r.t. and heated to approx. 30° C. until complete dissolution of the solid. The solution is cooled to r.t., then DTPM-reagent (3.5 g, 16.6 mmol) is added in one portion, and the stirring is continued at r.t. for 1 h. (After approx. 5 min. crystallization of the product starts.) The slurry is cooled to approx. 5° C., then kept at 5° C. for 2 h. The solid is filtered off (easy filtration on G3), washed with cold methanol (20 mL, 5° C.), then dried in a vacuum oven (30 mbar/40° C./12 h). Yield: 6.06 g (83%).

$^1$HNMR: 10.4 (dd, 1H), 8.15 (d, 1H), 5.30 (d, 1H), 4.85 (m, 1H), 4.68 (d, 1H), 3.75 (m, 2H), 3.51 (m, 1H), 3.41 (m, 1H), 3.27 (m, 1H), 3.15 and 3.14 (2×s, 3-3H), 1.61 (m, 1H), 1.43 (m, 1H), 1.23 (m, 24H), 0.84 (t, 3H).

$^{13}$C NMR: 163.97, 162.17, 159.2, 151.58, 89.23, 73.71, 70.71, 64.47, 59.03, 33.69, 31.26, 29.18, 28.9, 28.67, 27.32, 26.68, 24.85, 22.06, 13.92.

Example 2

Preparation of (2S,3R,4E)-3-O-benzoyl-2-N-((1,3-dimethyl-2,4,6(1H,3H,5H)-trioxopyrimidine-5-ylidene)methyl)-4-octadecene (2S,3R,4E)-2-NH-DTPM-4-octadecene-1,3-diol (10 g, 21.5 mmol) was dissolved in 50 mL dry dichloromethane (50 mL), then pyridine (13 mL) and trityl chloride (7.19 g, 25.8 mmol) were added and the reaction mixture was stirred at room temperature for 20 hours. Benzoyl chloride (3 mL, 25.8 mmol) was added to the reaction mixture and stirred at room temperature for additional 5 hours, then methyl alcohol (0.5 mL) was added. After 3 minutes stirring the reaction mixture was washed twice with 10% hydrochloric acid solution (2×30 mL). Methyl alcohol (8 mL) and p-toluene-suflonic acid monohydrate (0.76 g, 4 mmol) were added to the dichloromethane solution and the mixture was stirred under reflux for 16 hours. After cooling down to room temperature the slurry was washed twice with 5% $NaHCO_3$ solution (2×20 mL) and once with water (20 mL).

The organic phase was dried over $MgSO_4$, then concentrated in vacuo and the residue was crystallized from isopropanol. Yield: 10.13 g (83%)

$^1$H NMR (400 MHz, $CDCl_3$): 10.52 (dd, 1H), 8.24 (d, 1H), 8.02 (m, 2H), 7.59 (m, 1H), 7.47 (m, 2H), 5.95 (m, 1H), 5.65 (m, 1H), 5.53 (dd, 1H), 3.93-3.74 (m, 3H), 3.31 (s, 3H), 3.27 (s, 3H), 2.07 (q, 2H), 1.25 (m, 22H), 0.88 (t, 3H)

$^{13}$C NMR (400 MHz, $CDCl_3$): 165.68, 164.76, 162.97, 159.81, 151.94, 139.86, 133.62, 129.78, 129.36, 128.56, 122.49, 91.20, 73.38, 65.30, 61.29, 32.43, 31.90, 29.67, 29.64, 29.53, 29.43, 29.33, 29.13, 28.78, 27.83, 27.13, 22.67, 14.10

Example 3

Preparation of (2S,3R,4E)-3-O-benzoyl-2-N-((1,3-dimethyl-2,4,6(1H,3H,5H)-trioxopyrimidine-5-ylidene)methyl)-1-O-[2,3,6-tri-O-benzoyl-4-O-(2,3,4,6-tetra-O-benzoyl-β-D-galactopyranosyl)-β-D-glucopyranosyl]-4-octadecene (2S,3R,4E)-3-O-benzoyl-2-N-((1,3-dimethyl-2,4,6(1H,3H,5H)-trioxopyrimidine-5-ylidene)methyl)-4-octadecene acceptor (5 g, 8.776 mmol) and trichloroacetimidate 4-O-(2,3,4,6-O-tetra-benzoyl-β-D-galactopyranosyl)-2,3,6-tri-O-benzoyl-β-D-glucopyranoside donor (13.87 g, 11.41 mmol) were dissolved in 150 mL dry dichloromethane, then boron trifluoride etherate (0.5 mL, 4.388 mmol) was added and the reaction mixture was stirred at room temperature for 30 minutes. The reaction mixture was quenched by adding 5% $NaHCO_3$ solution (70 mL) and stirred at room temperature for 1 hour. The phases were separated, the organic phase was concentrated in vacuo and the residue was purified by column chromatography. Yield: 13.4 g (94%)

$^1$H NMR (400 MHz, $CDCl_3$): 10.35 (dd, 1H), 8.18 (d, 1H), 8.05-7.15 (m, 40H), 5.72-5.85 (m, 4H), 5.49-5.58 (m, 2H), 5.33-5.40 (m, 2H), 4.85 (d, 1H), 4.77 (d, 1H), 4.53 (m, 2H), 4.27 (m, 1H), 3.84-3.99 (m, 5H), 3.67-3.78 (m, 2H), 3.22 (s, 3H), 3.17 (s, 3H), 1.27 (m, 24H), 0.90 (t, 3H)

$^{13}$C NMR (400 MHz, $CDCl_3$): 165.63, 165.49, 165.36, 165.28, 165.16, 164.98, 164.73, 164.66, 162.46, 159.50, 151.90, 139.77, 133.49, 133.36, 133.13, 129.96, 129.83, 129.77, 129.72, 129.63, 129.51, 129.45, 129.36, 129.27, 129.10, 128.84, 128.64, 128.61, 128.55, 128.24, 121.64, 100.94, 100.43, 91.50, 75.57, 73.39, 73.26, 72.62, 71.74, 71.33, 71.25, 69.82, 67.44, 67.16, 62.79, 62.01, 60.93, 32.36, 31.89, 29.67, 29.63, 29.52, 29.37, 29.33, 29.11, 28.69, 27.66, 26.94, 22.66, 14.10

Example 4

Preparation of (2S,3R,4E)-2-N-((1,3-dimethyl-2,4,6 (1H,3H,5H)-trioxopyrimidine-5-ylidene)methyl)-1-O-[4-O-((β-D-galactopyranosyl)-( β-D-glucopyranosyl]-3-hydroxy-4-octadecene (2S,3R,4E)-3-O-benzoyl-2-N-((1,3-dimethyl-2,4,6(1H,3H,5H)-trioxopyrimidine-5-ylidene)methyl)-1-O-[2,3,6-tri-O-benzoyl-4-O-(2,3,4,6-tetra-O-benzoyl-β-D-galactopyranosyl)-β-D-glucopyranoside]-4-octadecene (10 g, 6.16 mmol) were added to dry methanol (200 mL) and 25% NaOMe in methanol (0.14 mL, 0.616 mmol) was added. The reaction mixture was stirred at room temperature for 2 days. The product crystallized out of the reaction mixture. The crystallization slurry was cooled down to 0-5° C., stirred at 0-5° C. for 2 hours. The solid was filtered off, washed with cold methanol (2×10 mL), then dried in a vacuum oven (30 mbar/50° C./12 h). Yield: 4.44 g (91%)

$^1$H NMR (400 MHz, DMSO): 8.19 (s, 1H), 5.63 (m, 1H), 5.36 (dd, 1H), 4.21 (m, 3H), 3.94 (m, 1H), 3.78 (m, 2H), 3.70-3.54 (m, 6H), 3.41-3.31 (m, 7H), 3.14 (m, 11H), 2.50 (s, 1H), 1.95 (m, 2H), 1.17 (m, 24H), 0.79 (t, 3H)

$^{13}$C NMR (400 MHz, DMSO): 166.18, 164.74, 161.50, 153.59, 136.30, 129.74, 105.34, 104.38, 91.65, 80.66, 77.21, 76.73, 76.46, 74.96, 74.72, 72.58, 70.28, 69.02, 65.95, 62.49, 62.03, 33.49, 33.15, 30.91, 30.89, 30.86, 30.84, 30.81, 30.78, 30.56, 30.41, 30.32, 28.37, 27.74, 23.85, 14.76

Example 5

Preparation of (2S,3R,4E)-2-amino-1-O-[4-O-(β-D-galactopyranosyl)-β-D-glucopyranosyl]-3-hydroxy-4-octadecene (2S,3R,4E)-2-((1,3-dimethyl-2,4,6(1H,3H,5H)-trioxopyrimidine-5-ylidene)methyl)-1-O-[4-O-(β-D-galactopyranosyl)-β-D-glucopyranoside]-3-hydroxy-4-octadecene (2 g, 2.532 mmol) and N,N-dimethyl-1,3-propanediamine (0.95 mL, 7.596 mmol) were added to 10 mL dry methanol. The reaction mixture was stirred at 60° C. for 3 hours, then at room temperature for an additional 12 hours. The product crystallized out of the reaction mixture. The crystallization slurry was cooled down to 0-5° C., stirred at 0-5° C. for 1 hour. The solid was filtered off, washed with cold methanol (2×4 mL), then dried in a vacuum oven (30 mbar/50° C./12 h). Yield: 1.43 g (90%)

$^1$H NMR (600 MHz, DMSO): 5.57 (ddd, 1H), 5.48 (dd, 1H), 5.28 (s, 2H), 5.08 (d, 1H), 4.78 (d, 1H) 4.67 (s, 1H), 4.66 (s, 1H), 4.65 (t, 1H), 4.56 (t, 1H), 4.51 (d, 1H), 4.20 (d, 1H), 4.17 (d, 1H), 3.8-3.73 (m, 3H), 3.61 (t, 1H), 3.60-3.52 (m, 4H), 3.48-3.45 (m, 2H), 3.32-3.28 (m, 5H), 3.02 (t, 1H), 2.76 (m, 1H), 1.99 (m, 2H), 1.40-1.15 (m, 24H), 0.85 (t, 3H)

$^{13}$C NMR (600 MHz, DMSO): 131.25, 131.05, 103.82, 102.676 80.67, 75.49, 74.81, 73.21, 73.09, 72.77, 71.26, 70.50, 68.09, 60.43, 60.35, 55.04, 31.75, 31.26, 29.02, 28.91, 28.84, 28.81, 28.67, 28.59, 22.06, 13.92

The invention claimed is:

1. A method for producing a glycosylated sphingoid base of General Formula XIX, XX, XXI, XXII, XXIII or XXIV, or a salt thereof:

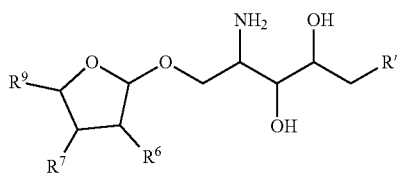

General Formula XIX

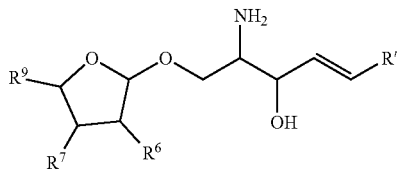

General Formula XX

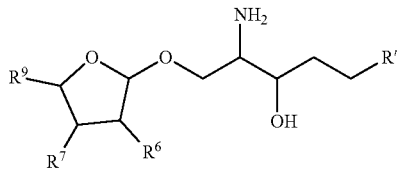

General Formula XXI

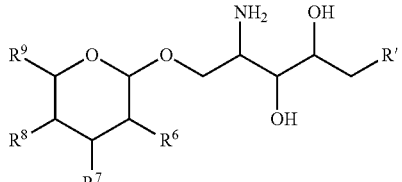

General Formula XXII

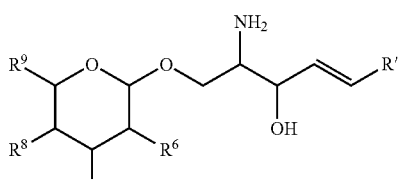

General Formula XXIII

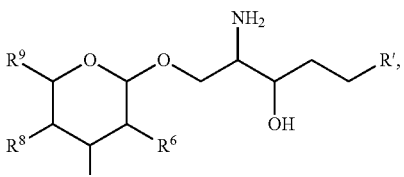

General Formula XXIV wherein
R' is H, aryl or an alkyl chain having 1-43 carbon atoms, which may be a straight chain or branched, and/or which may be saturated or contain one or more double bonds, and/or which may contain one or more functional groups, the one or more functional groups being selected from the group consisting of a hydroxyl group, an alkoxy group, a primary, secondary or tertiary amine, a thiol group, a thioether and a phosphorus containing functional group,
$R^6$ is H, OH, $NH_2$, $N_3$, NH-acyl or a carbohydrate moiety,
$R^7$ and $R^8$ are independently selected from H, OH or a carbohydrate moiety,
$R^9$ is H, $CH_3$, COOH, $CH_2OH$ or a $CH_2O$-carbohydrate moiety, and the dashed line ----- represents a hydrogen bond, starting from a sphingoid base of General Formula I, II or III, wherein the sphingoid base has an N-protecting group, wherein the N-protecting group is a vinylogous amide-type N-protecting group:

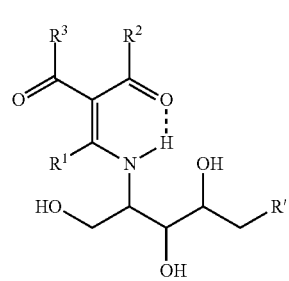

General Formula I

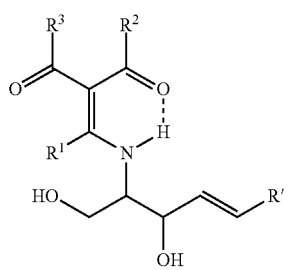

General Formula II

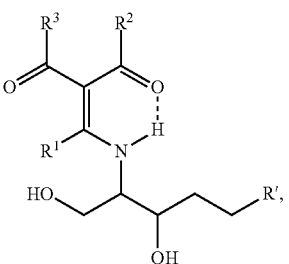

General Formula III wherein

R' is as defined above, $R^1$ is H, optionally substituted alkyl or optionally substituted aryl, $R^2$ and $R^3$ form a cyclic structure characterized by a 5-8-membered ring, and the dashed ----- line represents a hydrogen bond, this method comprising the steps of:

a) protecting the hydroxyl (OH) groups at $C_3$ and $C_4$ of General Formula I or at $C_3$ of General Formula II or III, respectively, with an O-protecting group, forming an O-protected compound, b) reacting the O-protected compound of step (a) as an acceptor molecule with a carbohydrate donor, wherein the carbohydrate donor comprises an optionally substituted furanose or an optionally substituted pyranose ring, wherein the optionally substituted furanose ring or the optionally substituted pyranose ring is covalently linked via either an alpha- or a beta-glycosidic linkage to the $C_1$—O group of the acceptor molecule, c) removing O-protecting group(s) from a compound formed in step (b), removing N-protecting group(s) from a compound formed in step (c).

2. A compound of General Formula IV, obtainable by step (a) of the method of claim 1:

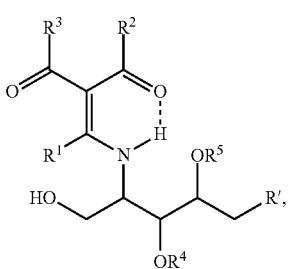

General Formula IV wherein $R^4$ and $R^5$ are independently selected from acyl, optionally substituted alkyl, optionally substituted acetal, optionally substituted ketal or silyl or wherein $R^4$ and $R^5$ form a cyclic structure.

3. A compound of General Formula V, obtainable by step (a) of the method of claim 1:

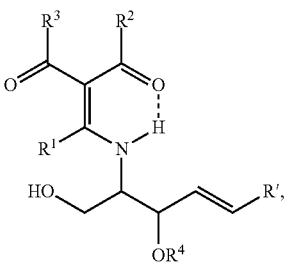

General Formula V wherein $R^4$ is acyl, optionally substituted alkyl, optionally substituted acetal, optionally substituted ketal or silyl.

4. The method of claim 1, wherein step (a) produces a compound of General Formula VI:

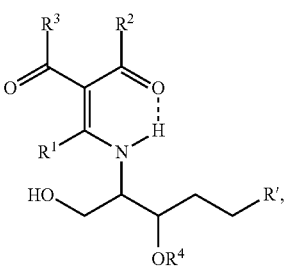

General Formula VI wherein $R^4$ is acyl, optionally substituted alkyl, optionally substituted acetal, optionally substituted ketal or silyl.

5. The method of claim 1, wherein steps (a) to (b) produce a compound of General Formula VII:

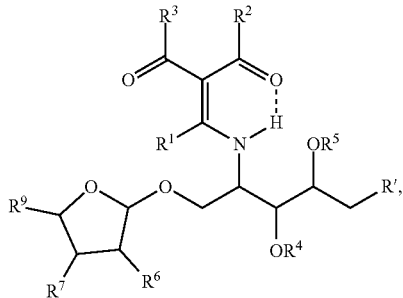

General Formula VII wherein
$R^4$ and $R^5$ are independently selected from acyl, optionally substituted alkyl, optionally substituted acetal, optionally substituted ketal or silyl or wherein $R^4$ and $R^5$ form a cyclic structure.

6. The method of claim 1, wherein steps (a) to (b) produce a compound of General Formula VIII:

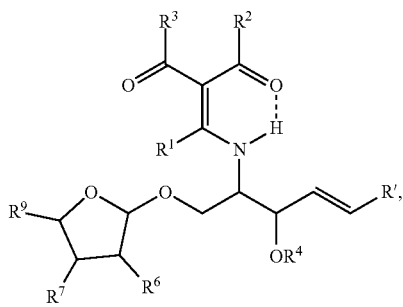

General Formula VIII wherein
$R_4$ is acyl, optionally substituted alkyl, optionally substituted acetal, optionally substituted ketal or silyl.

7. The method of claim 1, wherein steps (a) to (b) produce a compound of General Formula IX:

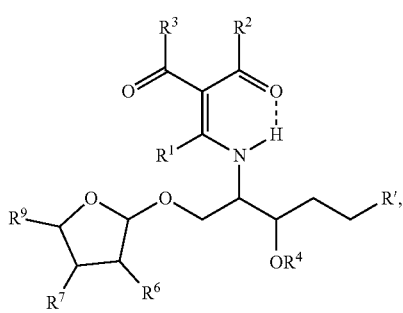

General Formula IX wherein
$R_4$ is acyl, optionally substituted alkyl, optionally substituted acetal, optionally substituted ketal or silyl.

8. The method of claim 1, wherein steps (a) to (b) produce a compound of General Formula X:

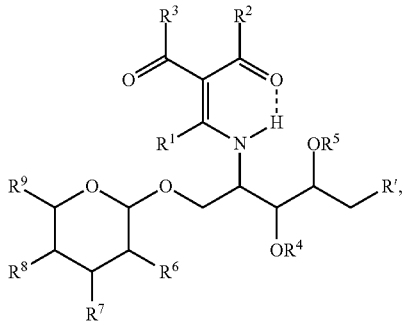

General Formula X wherein
$R^4$ and $R^5$ are independently selected from acyl, optionally substituted alkyl, optionally substituted acetal, optionally substituted ketal or silyl or wherein $R^4$ and $R^5$ form a cyclic structure.

9. The method of claim 1, wherein steps (a) to (b) produce a compound General Formula XI: obtainable by steps (a) to (b) of the method of claim 1:

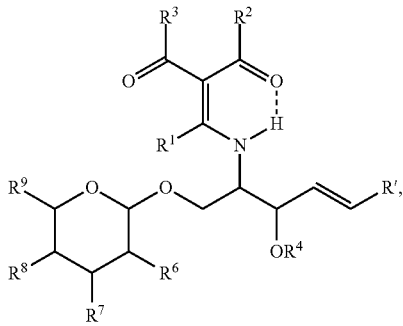

General Formula XI wherein
$R^4$ is acyl, optionally substituted alkyl, optionally substituted acetal, optionally substituted ketal or silyl.

10. The method of claim 1, wherein steps (a) to (b) produce a compound of General Formula XII:

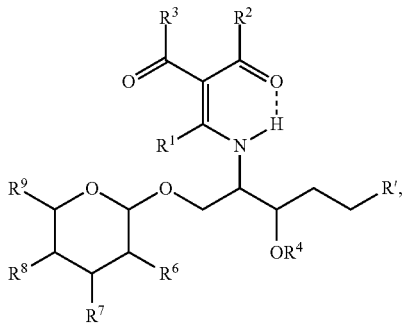

General Formula XII wherein

R$_4$ is acyl, optionally substituted alkyl, optionally substituted acetal, optionally substituted ketal or silyl.

11. The method of claim 1, wherein steps (a) to (c) produce a compound of General Formula XIII.

General Formula XIII

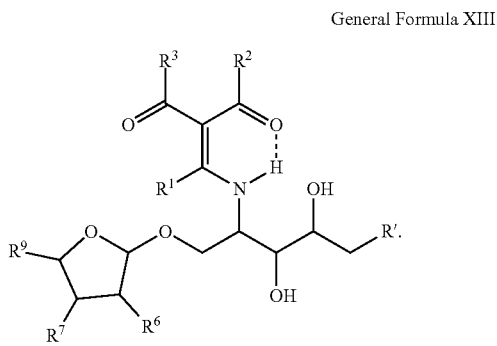

12. The method of claim 1, wherein steps (a) to (c) produce a compound of General Formula XIV:

General Formula XIV

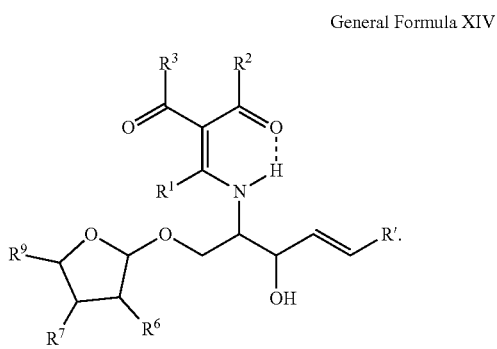

13. The method of claim 1, wherein steps (a) to (c) produce a compound of General Formula XV:

General Formula XV

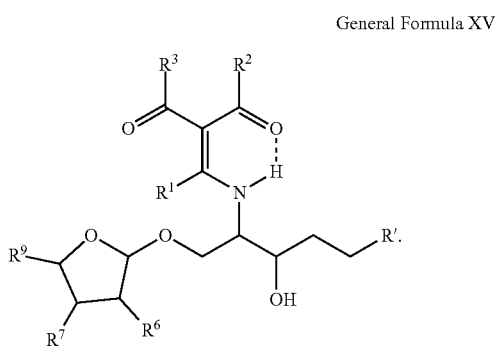

14. The method of claim 1, wherein steps (a) to (c) produce a compound of General Formula XVI:

General Formula XVI

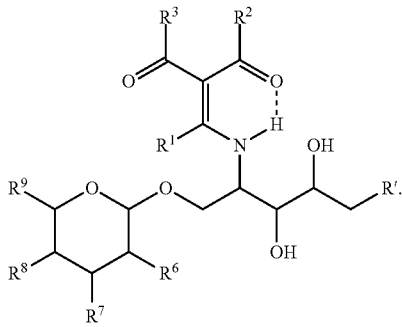

15. The method of claim 1, wherein steps (a) to (c) produce a compound of General Formula XVII.

General Formula XVII

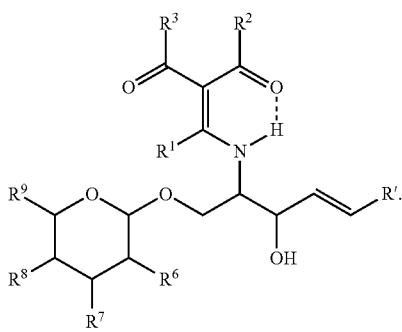

16. The method of claim 1, wherein steps (a) to (c) produce a compound of General Formula XVIII.

General Formula XVIII

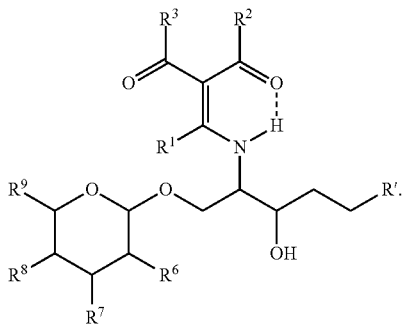

17. The method of claim 1, wherein the N-protecting group is 1,3-dimethyl-5-[(dimethylamino)mtheylene]-2,4,6 (1H,3H,5H)-trioxopyrimidine (DTPM).

18. The method of claim 1, further comprising:
producing 1-O-glycosyl-ceramide, 1-O-glycosyl-phytoceramide or 1-O-glycosyl-dihydroceramide by N-acylation of a glycosylated sphingoid base of General Formula XIX:

General Formula XIX
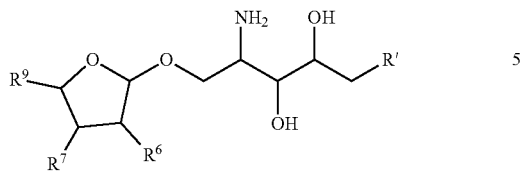
with an acyl moiety of a $C_{12}$-$C_{30}$ acyl group which can be saturated, unsaturated or optionally substituted via the use of the corresponding carboxylic acid, acid chloride, ester or anhydride in the presence of a base.
* * * * *